(12) United States Patent
Skulason et al.

(10) Patent No.: US 11,291,371 B2
(45) Date of Patent: Apr. 5, 2022

(54) METHOD AND MEANS TO MAKE INFRARED IMAGE OF THE FEMALE BREAST, OTHER HUMAN ORGANS AND OTHER OBJECTS

(71) Applicants: Gunnar Erik Skulason, Pleasanton, CA (US); Sergio Lara Pereira Monteiro, Los Angeles, CA (US)

(72) Inventors: Gunnar Erik Skulason, Pleasanton, CA (US); Sergio Lara Pereira Monteiro, Los Angeles, CA (US)

(73) Assignee: Sergio Lara Pereira Monteiro, Los Angeles, CA (US)

( * ) Notice: Subject to any disclaimer, the term of this patent is extended or adjusted under 35 U.S.C. 154(b) by 0 days.

(21) Appl. No.: 16/931,407

(22) Filed: Jul. 16, 2020

(65) Prior Publication Data
US 2021/0022612 A1    Jan. 28, 2021

Related U.S. Application Data

(60) Provisional application No. 62/874,903, filed on Jul. 16, 2019.

(51) Int. Cl.
*A61B 5/00*        (2006.01)
(52) U.S. Cl.
CPC ......... *A61B 5/0091* (2013.01); *A61B 5/0075* (2013.01); *A61B 5/4887* (2013.01); *A61B 5/7425* (2013.01)

(58) Field of Classification Search
CPC ... A61B 5/0091; A61B 5/0075; A61B 5/4887; A61B 5/7425; A61B 5/6823; A61B 2562/0238; A61B 2562/046; A61B 5/0035
See application file for complete search history.

(56) References Cited

U.S. PATENT DOCUMENTS

| | | | | |
|---|---|---|---|---|
| 5,413,098 A * | 5/1995 | Benaron | ............ | A61B 5/14542 250/332 |
| 5,803,082 A * | 9/1998 | Stapleton | ............. | A61B 5/0091 600/407 |
| 5,876,339 A * | 3/1999 | Lemire | ................ | A61B 5/4312 600/425 |
| 6,122,542 A * | 9/2000 | Lee | ...................... | A61B 6/0414 600/427 |
| 8,788,017 B2 * | 7/2014 | Yu | ........................... | A61B 6/00 600/411 |
| 9,492,089 B2 * | 11/2016 | Hielscher | ........... | A61B 5/02007 |

(Continued)

*Primary Examiner* — Serkan Akar

(57) ABSTRACT

A device to measure with infrared radiation, then make a projection picture of, blood concentration inside the body of animals. Blood concentration in cancer masses increases, when compared to adjoining tissues, as flesh and bones, also with a disorganized capillary distribution. The device disclosed in this invention makes two types of images, a first image, which we call transmitted image, with infrared radiation that suffered no scattering as it propagates through the body or part of the body, and a second image, which we call scattered image, with radiation that suffered one or more scattering events, as it propagates through the body. Finally, a third image can be made from a combination of the first and second image after a suitable mathematical manipulation of the first and/or second images. Each of the three images may be used as an indication of cancer.

5 Claims, 8 Drawing Sheets

(56) References Cited

U.S. PATENT DOCUMENTS

Figure 1A:
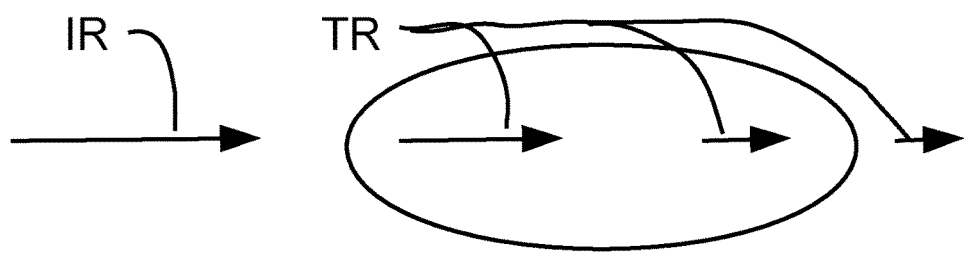

| | | | |
|---|---|---|---|
| 2010/0081922 A1* | 4/2010 | Schipper | A61B 5/0073 |
| | | | 600/425 |
| 2010/0272331 A1* | 10/2010 | Brendel | A61B 5/0091 |
| | | | 382/128 |
| 2014/0236003 A1* | 8/2014 | Hielscher | A61B 5/708 |
| | | | 600/428 |
| 2014/0350358 A1* | 11/2014 | Oikawa | A61B 8/4494 |
| | | | 600/301 |
| 2015/0119665 A1* | 4/2015 | Barbour | A61B 5/14552 |
| | | | 600/328 |
| 2015/0182121 A1* | 7/2015 | Barbour | A61B 5/7282 |
| | | | 600/425 |
| 2016/0066793 A1* | 3/2016 | Yamamoto | A61B 5/4312 |
| | | | 600/407 |
| 2017/0303792 A1* | 10/2017 | Nagao | G01S 15/8965 |
| 2019/0183349 A1* | 6/2019 | Miyasato | A61B 8/13 |

\* cited by examiner

METHOD AND MEANS TO MAKE INFRARED IMAGE OF THE FEMALE BREAST, OTHER HUMAN ORGANS AND OTHER OBJECTS

CROSS-REFERENCE TO RELATED APPLICATIONS

This application is related to the famous U.S. Pat. No. 5,590,169, entitled "Radiation imaging system", issued Dec. 31, 1996 to Sergio Lara Pereira Monteiro. It is also related to applied Ser. No. 12/586,562, filed 2009, September 24, entitled "Method and means for connecting a large number of electrodes to a measuring device", applied Ser. No. 12/586,763, filed 2009, September 28, entitled "Method and means for connecting and controlling a large number of contacts for electrical cell stimulation in living organisms", and applied Ser. No. 12/657,393, filed 2010, Jan. 20, entitled "Method for transferring images with incoherent randomly arranged fiber optical bundle and for displaying images with randomly arranged pixels", and applied Ser. No. 13/053,137, filed 2011, March 21, entitled "Method and means to address and make use of multiple electrodes for measurements and electrical stimulation in neurons and other cells including brain and heart", which are incorporated by reference in their entirety.

This invention relates to method and means to screen for cancer and also to act as an accessory to confirmation of cancer detected by other means, as breast screening with mammography (X-ray) and ultrasound. This invention discloses a method and a means to use infrared radiation (also known as infrared light or simply infrared) to detect the possible presence of cancerous mass, it being based on the detection of the increased blood supply at the suspicious volume, which occurs as a consequence of a process known in medicine as angiogenesis. Infrared radiation is preferable for the device disclosed in this patent application, but ordinary red light, particularly what is known in optics as deep red (at the end of the visible spectrum, near in wavelength and photon energy to the infrared) is also a possibility. Red visible light offers the advantage of easiness of work, when compared with the infrared light, because the operator can see the beam directly, which is not possible when the device operates with infrared radiation, which is invisible for humans, so the operator must rely exclusively on what is displayed on a (computer) monitor screen.

This invention relates to infrared images (by this we mean images obtained with infrared radiation, a convention we will be using throughout this patent document), as opposed to visible light images. The more correct name "infrared radiation" is often avoided due to the large number of people that gets afraid of the word "radiation", which is likely to be the reason why infrared radiation is also known as infrared "light", which is an incorrect word in this case but a word that is sometimes used to avoid scaring people with the word "radiation", which here is used with its physics meaning of electromagnetic radiation. In physics, electro-magnetic radiation encompass anything from radio waves, microwaves used for cooking, infrared, ordinary visible light, ultra-violet, X-ray and gamma-rays. When we mention infrared radiation it has nothing whatsoever to do with ionizing radiation, which is cancer causing, generally speaking being the photons carrying energy equal to or larger than ultra-violet photons. So dear reader, though the inventors will avoid the use of radiation in this document, it may enter here occasionally, and when it happens it has nothing to do with cancer-causing photons.

The images we are referring here includes images of parts easily accessible, as the women's breast (well, not so widely accessible . . . ), and also other parts inside the body, as prostate, colon, stomach, esophagus, brain, and more, all organs more or less accessible from some existing opening, as the anus, the urethra, the esophagus, the ear, respectively, etc. via In particular, this invention relates to images of body parts made with infrared radiation (or infrared "light"), which are valuable as an indicator of cancer, because cancerous masses necessarily develop new blood vessels to increase the blood and nutrients supply to the growing mass, a process known in medicine as angiogenesis. Consequently, to look for excess blood is a way to look for a cancerous mass. In other words, our invention uses the difference of the infrared properties between blood and other tissues. infrared radiation has different optical properties for blood than for flesh and bones, which, in turn, causes that blood can be distinguished from flesh and bones with infrared radiation. This last statement is familiar to persons that work in this field and we want to point it out to the reader that this last statement is similar to what our eyes do to detect any object in our surrounding: the colors that they reflect and absorb, their textures, etc. We do this all the time in our lives. Accordingly, to detect blood with the eye and visible light, for example, we use the fact that blood reflects red while absorbing orange-yellow-green-blue-violet. We normally use the detection of blood on the skin as an indicator of some cut, and then use the amount of blood as an indicator of the depth of the cut and the severity of the injury. Our invention is similar to this, only that it preferably uses infrared radiation, which is invisible to the eye, so the image has to be obtained with some infrared detector. In this patent application we disclose method and means that also allows for the detection of cancer in the prostate, in the stomach, in the colon, etc., using different wavelengths, and using particularly infrared images of these and other organs, as is with the objective of determining the possibility of cancerous masses in it.

FEDERALLY SPONSORED RESEARCH

Not applicable.

SEQUENCE LISTING OR PROGRAM

Not applicable.

BACKGROUND OF THE INVENTION

Field of Invention

This invention relates to images of parts of objects which are not directly accessible for visual inspection, as the inside parts of animals, and more particularly to image of the female breast, the head of infants, the male penis, teeth, and particularly to infrared images of the female breast and other male and female organs, with the objective of determining the possibility of cancerous masses in it. Similar method may be used with red light or other wavelengths as well.

It is known that near infrared radiation penetrates much deeper into human tissues/cells than visible light does (Ref: Valery Tuchin (Saratov State University "Tissue Optics—Light Scattering Methods and Instruments for Medical Diagnosis" SPIE Press, (2000)). The maximum infrared penetration is in the window from 750 nm to 1050 nm, known as near infrared, with a peak around 850 nm. Also, in this wavelength range, scattering is roughly 100 times stronger than absorption:

sigma-scatt=100×sigma-abs where sigma stands for cross-section, the physics name for what is known in most other fields as "probability of" (scattering or absorption in this case). It follows that most of the propagating beam (of infrared radiation) in animal cells is lost for imaging due to scattering, not due to absorption. This scattering, in turn, increases the path length, which then increases the probability of eventual absorption. For visible light in animal cells absorption dominates, so the propagating beam is lost due to absorption in most of the visible wavelength range (violet through beginning of red), though the increase of sigma-scatt starts in the red, having already an effect in the deep red, say, lambda>=700 nm.

This last statement is what is responsible for the redish color which one sees through a thinner part of our bodies, as the ear or the membrane between our fingers, against a bright light behind it, as the sun, which usually fascinates many children (it did fascinate me). When I was young I thought that I was seeing my own blood; now I know that what I saw then, and now, is the remaining light that is not absorbed by the thin path on the flesh, all the shorter wavelength radiation being absorbed (violet through orange), only the red, longer wavelength radiation remaining in the transmitted beam. Of course that the infrared is also there too, and much "brighter" than the red, but we just cannot not see it!

An infrared image is an extreme case of how one can see a person in a shower behind the usual frosted glass or plastic, which scatters the light, therefore destroying the image details. Our patent discloses methods to extract information from photons that have been subjected to such a process, akin to reconstructing the image from a person inside a shower stall, behind a frosted glass or plastic.

Definitions

We start with a definition of the most important terms used in this document, in order to comply with the requirement of making a complete description of the invention, including no doubts about the meaning of the terms used. Some of the terms in this definition section are used in the same meaning as normally accepted by workers in the field, and we include here if they are important enough for the understanding of the invention. Other terms are not well defined in the field of the invention, and our definition section makes it clear what we intend to mean, and still other terms may be of our introduction because they are specific to our invention.

Anatomical Planes.

(1) transverse or axial plane: for a vertically standing human facing the viewer, with its main axis along the vertical direction, a transverse or axial plane is any plane that is perpendicular to the human's main axis. In normal parlance this plane is called a horizontal plane.

(2) sagittal plane: We are going to use the term as it appears to be used by most people today, meaning the combination of the true sagittal plane and all the parasagittal planes. It is our interpretation that originally the sagittal plane was only the front-to-back longitudinal vertical plane that divides a [human] body standing in the vertical direction into right and left halves, and all other planes parallel to this true sagittal plane were the para-sagittal planes. Repeating, we are here using the term as it appears to be the current usage, that the one single sagittal plane and all the other planes parallel to it are called sagittal planes (3) coronal or frontal plane: is a plane passing through a standing human that contains vertical lines and is perpendicular to both the transverse and the sagittal planes. Looking at the human from the front, a coronal (frontal) plane is a flat plane facing the viewer.

Cross section. In physics this term is approximately equivalent to "probability", mostly the difference being that probability is normalized to 1 (that is, it is a number between zero and one) while cross section is not normalized to 1 (one) as probability is. The term stands to indicate the relative area of an obstacle that would interact with the propagating particle, so, the larger the cross section means the larger is the area, and therefore the larger is the probability of interaction.

Detector (central detector). We define the pixel of the detector array that lies along the direction of an incident radiation beam as "central detector" (CD in figures). The basis for the name is that the collection of data for the image reconstruction centers around the direction of the incident beam. (cf. with outlaying detectors). Engineering compromise needs to be made with this definition, and we define as central detector a group of pixels that either encompass the actual size of the incident beam if it suffered no scattering, because the actual initial beam may be larger than one single pixel on the CCD detector array, or because of the uncertainty on the position of the incident beam. If the later, the most central detectors would be considered the central detector(s), with the very near neighbors to it being neither central nor outlaying detectors. This and other possible approximations may be implemented without changing the general principles described in the patent application document. In some variations, the detector may be not a CCD array detector but be instead a few, two or more detectors, with a single detector aligned with the initial direction of the incident infrared beam, which is the central detector. This central detector is the radiation detector that measures the radiation that allows the construction of the image created with the non-scattered radiation, which we call transmitted radiation, which then is used to form the transmitted image.

Detector (outlaying detector). We define all the pixels of the detector array that lie around the direction of the incident beam as "outlaying detectors" (OD in figures). In some cases some detector pixels just around and next to the central detector may be disregarded, in which case the outlaying detectors start from a certain distance away from the central detector. This and other engineering approximations are considered part of the invention. (cf. with central detector). In some variations, the detector may be not a CCD array detector but be instead a few, two or more detectors, with one or more detectors positioned at an angle with the initial direction of the incident infrared beam, which is (are) the outlaying detectors, that is, the detectors that measure what we define as the scattered radiation, the detectors that measure the radiation for what we call scattered image.

Light ray. We are using this expression in the way it is popularly understood, which corresponds approximately to I. Newton's understanding of light. For us here in this document, light ray means the direction of propagation of one of several photons propagating within a small diameter beam along the same direction, including the energy carried by them. In fact there exists no light ray but rather the direction of propagation of an electromagnetic wave, but we will use the term this way to make our explanation here more widely available—according to the requirements of the USPTO. The electromagnetic radiation beam used for the device disclosed in this patent application is loosely speaking a light ray, because its transverse dimension (diameter) is much smaller than the other dimensions of the system.

Scattered image. We are defining scattered image as the image obtained from the information carried by all photons that have suffered at least one instance of scattering, and consequently propagate at a direction which makes an angle with the direction of the incident infrared beam. In the case of the main embodiment of the invention, where the photons are infrared and the medium of propagation is a human body, the probability of scattering is high enough that most scattered photons that propagate through the body have suffered many scattering events. For technical reasons, scattering is generally separated in two groups: forward scattering and backward scattering. The former (forward scattering) involves photons that have been deflected from 1 degree to 89 degrees, while the latter (back-scattering) involves photons that have been deflected from 91 to 180 degrees. These duality is artificial though, and only reflect other matters then the existence of photons at all angles (they do exist).

Scattered radiation. Radiation that has suffered at least one episode of scattering (direction changing).

Transmitted image. We are here defining this term in a more restricted meaning than the meaning of transmission. We are defining transmitted image as the image obtained with photons that have propagated through the body without absorption and without scattering: photons that propagated all the way to the detector along the initial direction of emission. Note that this is a definition of our own and an unorthodox use of the word as well. Another alternative way to look at the transmitted image, as we define it, is that the transmitted image is the image made by the photons that emerge on the distal side of the object (the patient, usually) along the same direction of propagation as the incident photon. Of course that these two definitions are mutually inconsistent, because a photon may suffer three scattering events, emerging after the third scattering along the same direction as the incident beam. This is a low enough probability event that it can be disregarded with undetectable error on the definition, an error below the detectable image quality. Consequently the two definitions are consistent within an engineering approximation, while they are inconsistent from a mathematical, geometrical, and logical point of view.

Transmitted radiation. In this patent application we are using the term in a non-traditional way as well, meaning the radiation that propagates through the object (the patient, usually) without any scattering event or absorption. Thus the transmitted radiation is the radiation that propagates along its initial direction of propagation onto the detector beyond the object. See transmitted image.

BACKGROUND

Discussion of Prior Art

There exists a great interest in inspecting unaccessible regions of objects or things, whether it be the inside of a car engine or the inside of a person. Accordingly, many methods have been developed for this purpose.

One possible way to classify the methods to inspect hidden parts, is to separate them by the means to illuminate them and by the means to bring the image out. Generally, inside parts do not receive natural illumination (if light were able to get in, it would also be able to get out and the inside would be visible!), so a method is needed to bring light in, before even considering the possibility of taking the image out. Earlier generations were limited to candlelight, which produces too faint light for good illumination, but even then, given the need to look at the inside of the human body, physicians have used it already in the 1800s. Today we have far brighter sources, more than enough to illuminate most objects one can imagine, probably any one in any situation.

The second class of problem, which is how to take the image out of a hidden part, can be tackled in more ways, and has, accordingly, many more solutions than the illumination part. Our invention relates to this: how to take images out of a hidden object with particular emphasis in infrared images—but not restricted to infrared by any means. Our invention is not limited to infrared, being applicable to other regions of the electromagnetic spectrum, and also to pressure waves, as sound waves, and other types of waves. Our invention is also applicable to the use of several photon energies (or several wavelengths), as infrared and visible and ultra-violet. Different wavelengths may produce different information, which are complementary, because different wavelengths have different penetration in the object and therefore they may carry information that is different and complementary. For example, ultra-violet and most visible light have virtually no penetration in animal cells, while infrared penetrates several centimeters beyond the incidence point into a body of animal cells.

Earlier attempts to look at hidden parts of an object were restricted to periscope type of devices, of the type used in submarines. These were devices with an system, usually a lens system with some mirrors, to form an image, then a tube, inside which the "light rays" had to propagate without hitting the walls of the pipe, then another lens optical system at the viewing side, which formed an image for human observation or photography. In recent times, with the advent of fiber optics, these devices could be made of much smaller diameter and also flexible, making use of optical fibers, which greatly improved the range of their use.

Most of the imaging systems that use fiber optics, use a bundle of fibers. The cost of the fiber optical bundle has been substantial part of the total cost of such fiber based observation systems, because the traditional method is to use what is known in the trade, though using a most infelicitous word in optics, a coherent bundle. By coherent bundle the practitioners of the art of taking an image out of an inaccessible place to another, more accessible place, mean a bundle of optical fibers (or hairs, since each fiber is the diameter of a hair) which is identically positioned in relation to each other at both extremities of the bundle. This severe restriction on the bundle to take the image out of an inaccessible place has been relaxed with the use of computers to correct for the shuffling of the fiber hairs in a bundle which is not coherent.

One of the many possible applications of the retrieval of an image of something hidden inside a human body, and a problem that has received much attention from the medical community, is the earlier detection of breast cancer in female human beings. Breast cancer is one of the most common forms of cancer in female humans, its incidence increasing with age. A possible test for breast cancer, which is valid for any other type of cancer too, is to measure a local increase in blood irrigation, which is known as angiogenesis. This is so because any cancer needs blood to bring nutrients to the fast growing cancerous cells, and until this need is satisfied, no cancer can possibly grow beyond 2 mm (millimeters) to become a life threatening mass. This 2 mm distance is the distance that nutrients can move from a capillary vessel to cells not in direct contact with capillary vessels. It happens that the blood vessels that grow to feed the cancerous mass is most often also disordered in organization, which is another indicator for the pathologist. Disordered organization here means that the blood vessels growing from cancer-caused angiogenesis do not decrease in diameter as they move away from the arteries then the reverse towards the heart, increasing in diameter as the blood is collected back to the heart into the veins. This disordered capillary growth from cancerous angiogenesis also causes uneven blood flow, flowing in both directions within each pumping cycle (diastole and systole and in-between). This let us say "crazy flow" (our word, not sanctioned by the medical profession!) occurs because, as written above, most often the capillaries that grow from cancer fail to follow the normal sequence of larger-to-smaller vessels at the pumping side (arterial blood) and smaller-to-larger vessels at the return side (venal blood). This to-and-from flow, in turn, causes that the blood in and near the cancerous mass is less capable of bringing nutrients to the cancerous mass, which in turn causes the cancer to request more angiogenesis, etc. Ultimately cancerous masses are more perfused by blood than normal, non-cancerous tissues. Since no cancer can grow in the absence of angiogenesis, any method that detect angiogenesis can function as an early cancer detection method. Our method of cancer detection is one such: a method to detect angiogenesis based on the optical property of blood, namely its higher absorption and scattering cross section (probability) to infrared radiation, when compared with most other cells that make the human body. Infrared is more useful for this, also because it has a high enough transmissivity, that the minimum necessary number of photons can propagate through a few cm (a few inches) of tissue, which is not the case for green or blue visible light.

BACKGROUND

Objects and Advantages

Accordingly, several objects and advantages of my beautiful invention are to offer an independent probe for the existence of cancerous masses in the female breast or other inner parts of the human body, that happen to be capable of being "illuminated" by an infrared beam which can then be detected beyond the cancerous mass (say, the female breast) after propagating through the cancerous mass. We will use the female breast as an example, but the same method can be applied to other parts of the human body with small modifications.

Another objective and advantage of my fantastic invention is to offer a method and a means to detect possible cancerous mass on superficial layers accessible to our device, as the colon (colonoscopy), stomach (from the mouth and esophagus), the lung (from the mouth and traquea), the bladder (from the urethra), the prostate (from either the urethra or the anus) the skin, etc.

Another objective and advantage of my fantastic and beautiful invention is to offer an independent method and means to detect possible cancerous masses, detecting the presence of angiogenesis, that is, the growth of blood vessels that characterizes cancer growths.

It is one object of this invention to provide images with better resolution (i.e., more visible spacial details) than existing systems.

It is a further object of this invention to provide images capable of detecting increase in blood supply for a region in the body, as part of a female breast, male penis and human (male and female) tongue, which is one of the characteristics of cancerous growth.

It is a further object of this invention to provide images with better resolution of the brain of a living animal as it functions, particularly images of the blood supply, which changes during mental processes. Such images can give information about the localization of thought process in the brain.

It is a further object of this invention to provide images capable of detecting changes of the oxygenation state of the hemoglobin in the blood as it flows through the brain, which is a marker of mental activity.

If one or more of the cited objectives is not achieved in a particular case, any one of the remaining objectives should be considered enough for the patent disclosure to stand, as these objectives are independent of each other.

Main embodiment—first application

SUMMARY

The main embodiment of the invention discloses a method and means to detect increased blood supply on particular regions of the female breasts, with respect to adjoining tissues around it. These regions characterized by increased blood supply are, in turn, suspicious of being cancerous. The increased blood supply may also be used to detect cancer on other internal parts of animals, as humans, which are accessible to inspection via image transmission and/or scattering, as by optical fiber bundles (coherent or incoherent), and/or CCD or other pixelized detectors that are capable of producing an image of the type produced by a digital camera, and of one or more individual "light" detectors. Image can be made using transmitted radiation that suffered no scattering event (which I call transmitted radiation here, a personal use of the word, see definition above) and using scattered radiation, both forward and backward scattering. The invention uses the differential transmission and scattering properties of blood cells, when compared with other cells, as muscles and bones, and the known fact in the field of oncology that cancerous masses have a larger blood supply when compared with non-cancerous tissues, due to a process known as angiogenesis.

DRAWINGS

FIG. 1A. Transmitted radiation

Figure 1B:
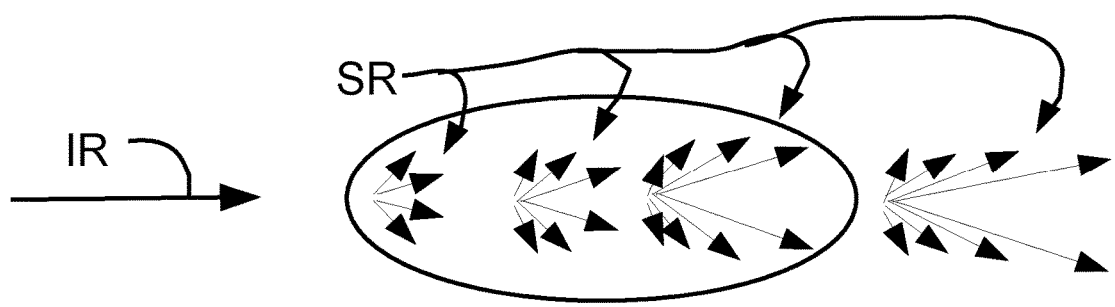

FIG. 1B. Scattering events.

Figure 1C:
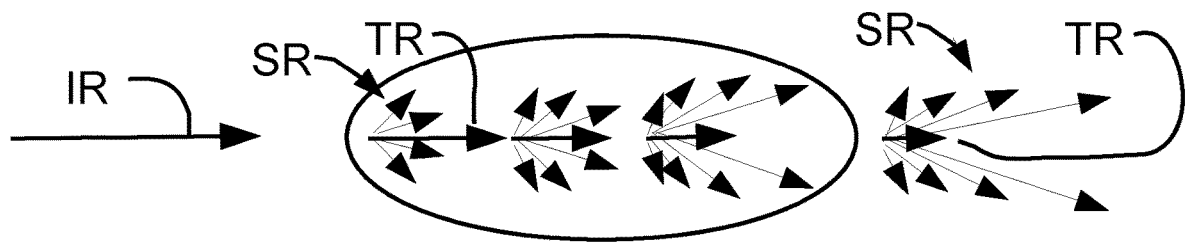

FIG. 1C. Mixed transmitted and scattering events.

Figure 2:
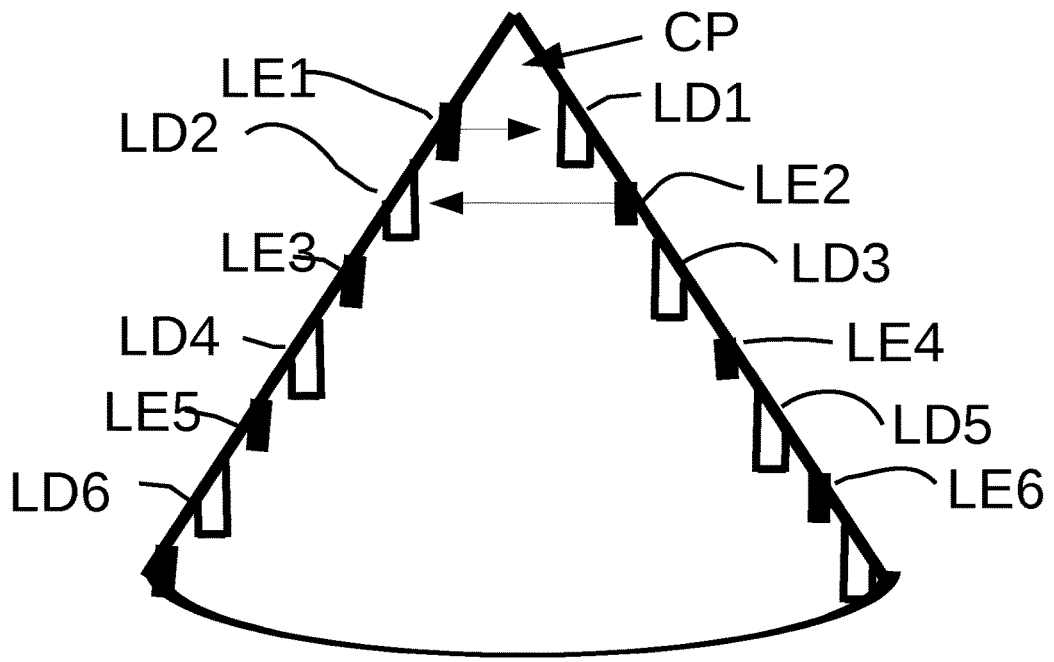

FIG. 2. The preferred embodiment of the breast cup of our invention. Cup (CP) of our invention with light emitters (LE) and light detectors (LD) in the inner face of the cup of our invention, also showing the direction of light from LE.

Figure 3:
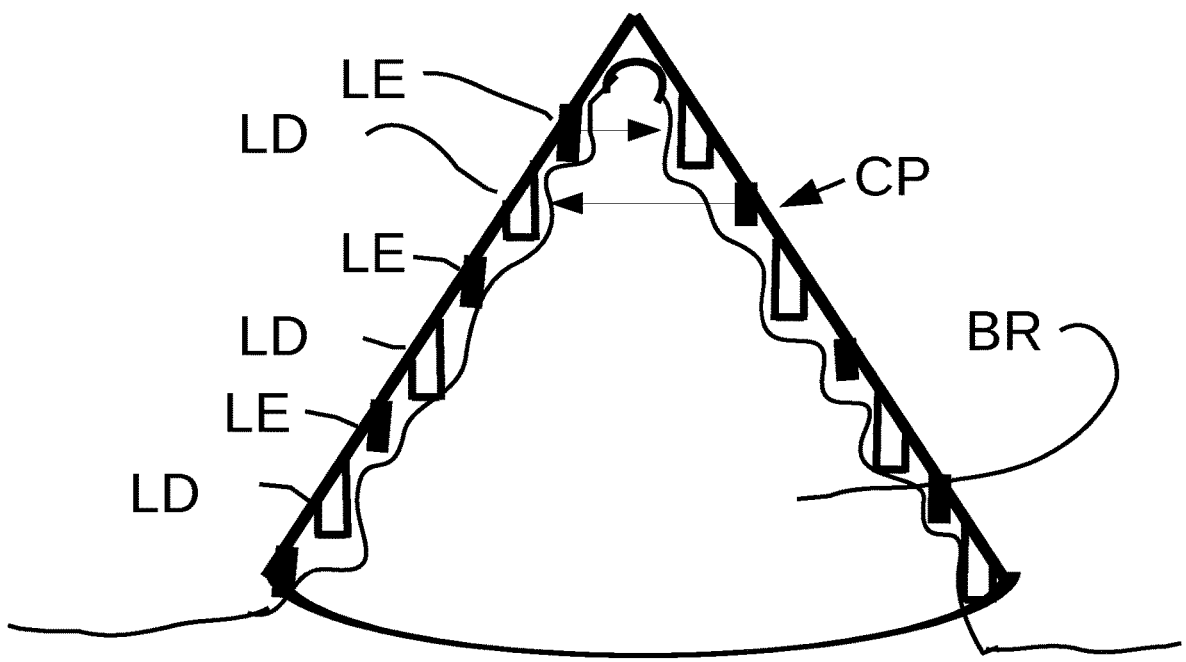

FIG. 3. Another view of the preferred embodiment of the breast cup of our invention also including a female breast in which the breast cup is inserted.

Figure 4:
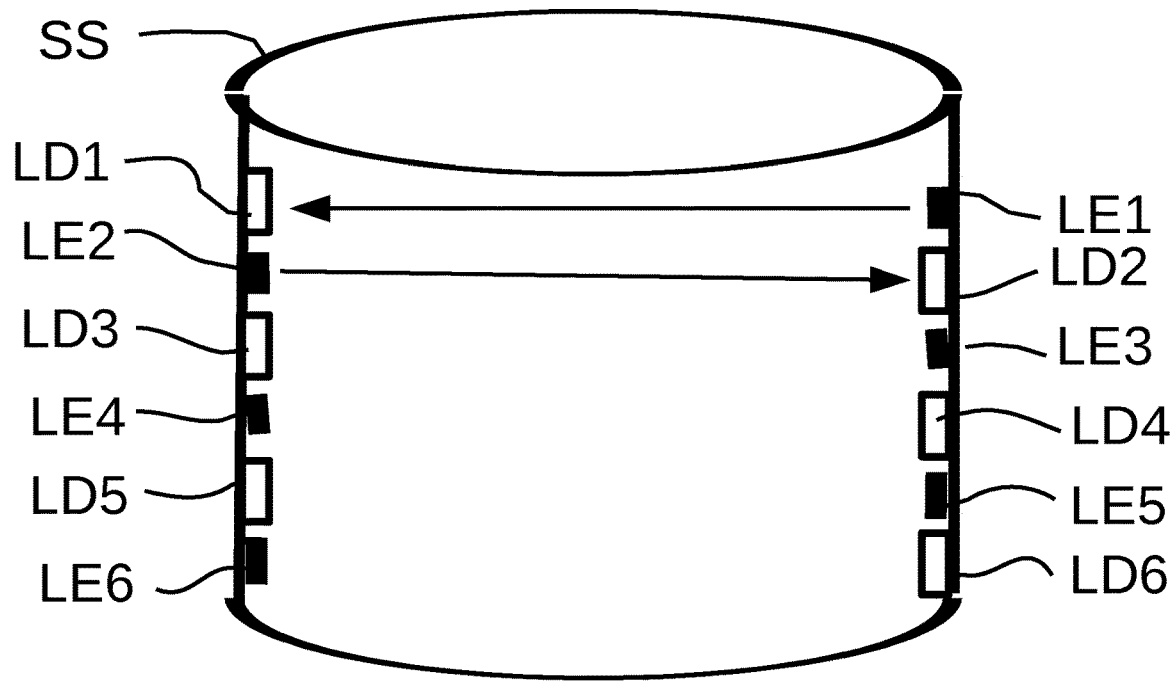

FIG. 4. Supporting Structure (SS) of our invention with light emitters (LE) and light detectors (LD) in the inner face of the SS of our invention, also showing the direction of light from LE.

Figure 5:
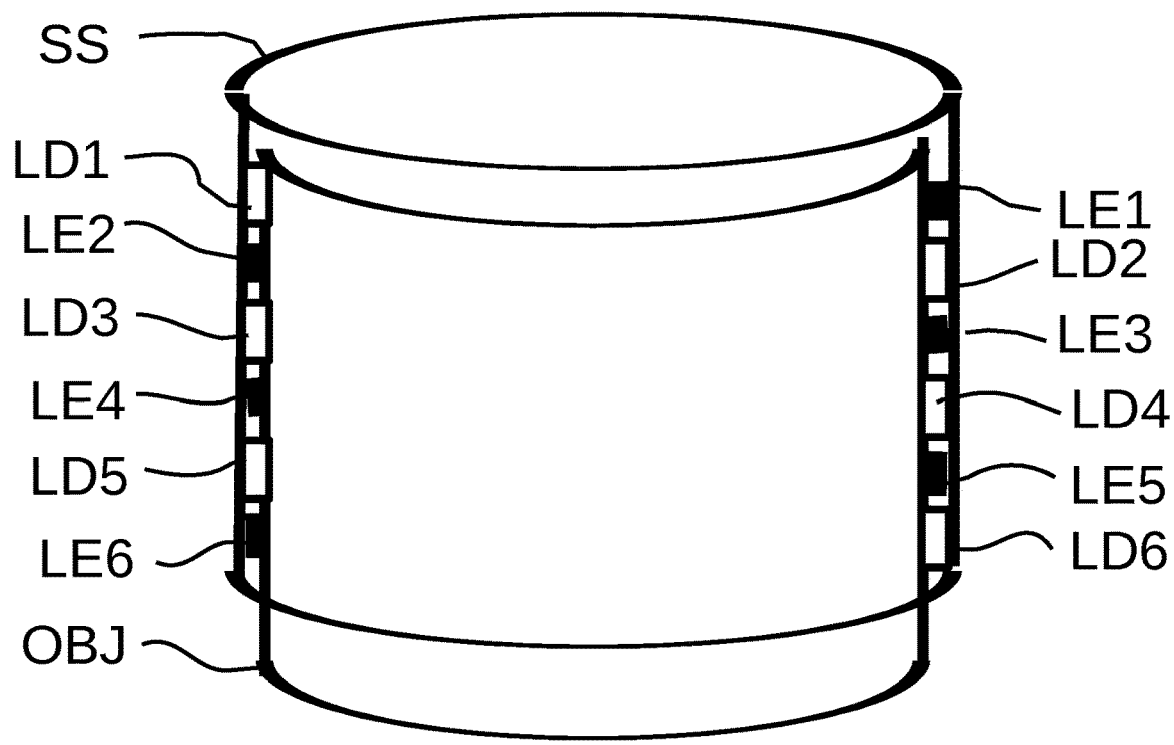

FIG. 5. Supporting Structure (SS) of our invention with light emitters (LE) and light detectors (LD) in the inner face of the cup of our invention covering an object (OBJ).

Figure 6:
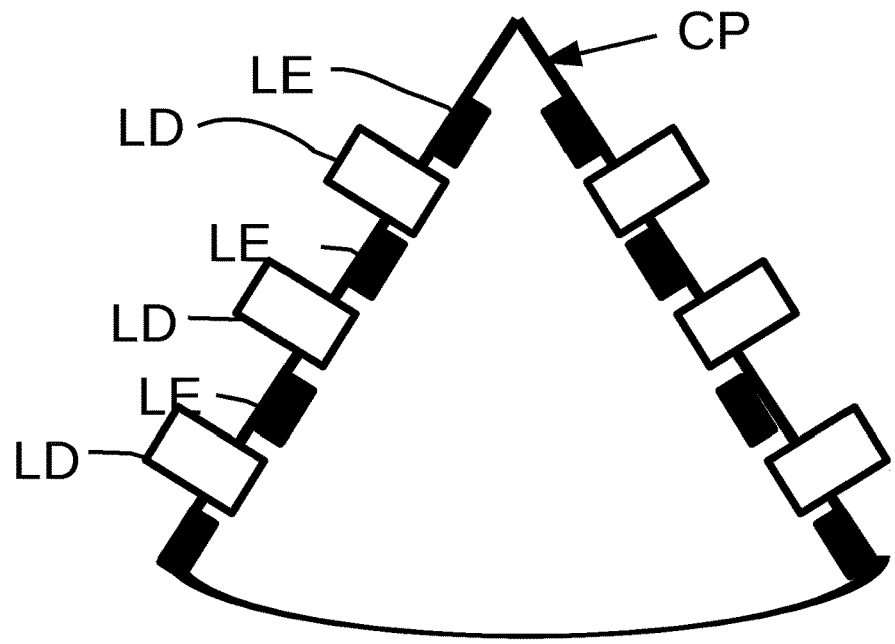

FIG. 6. Cup (CP) of our invention with light emitters (LE) and light detectors (LD) with collimators in the inner face of the cup of our invention.

Figure 7:
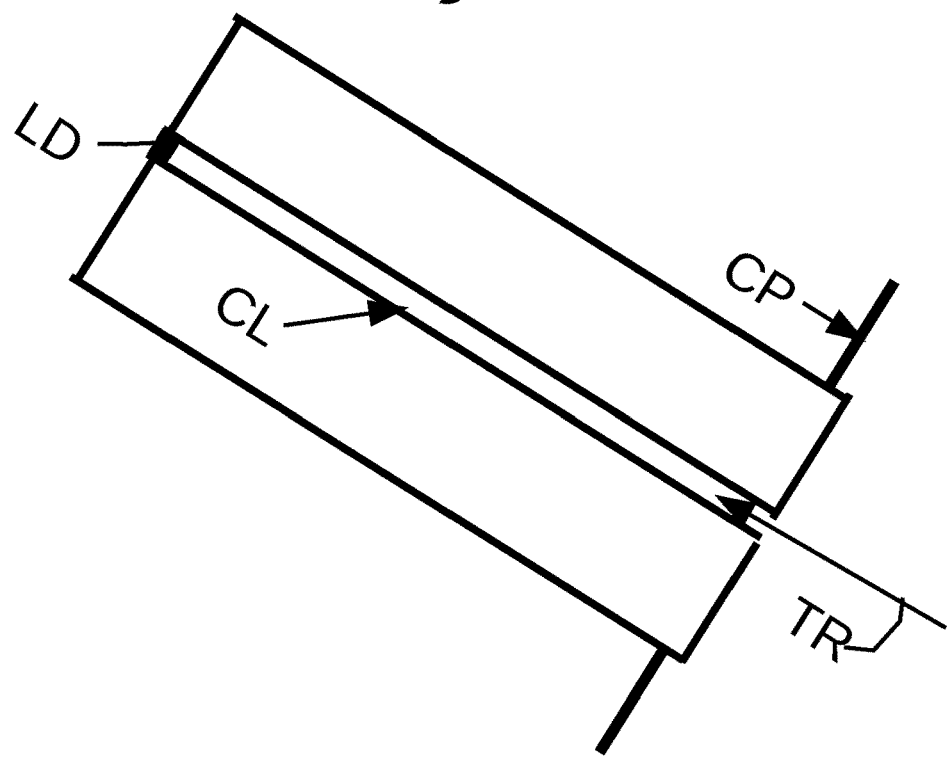

FIG. 7. Detail of collimator attached to light detectors LDs Light along the correct direction TR for transmission reaches light detector LD, else it is absorbed by collimator CL walls FIG. 8. Cup (CP) of our invention with light emitters (LE) and light detectors (DET) in the inner face of the cup of our invention.

Figure 9:
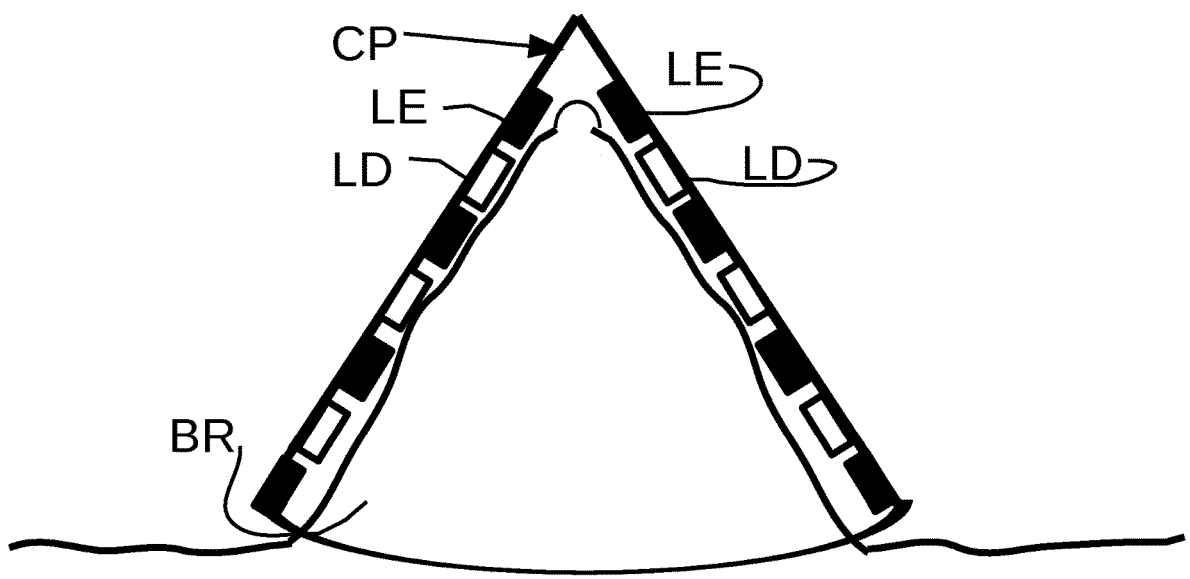

FIG. 9. Cup (CP) of our invention with light emitters (LE) and light detectors (DET) in the inner face of the cup of our invention covering a women's breast (BR)

Figure 10:
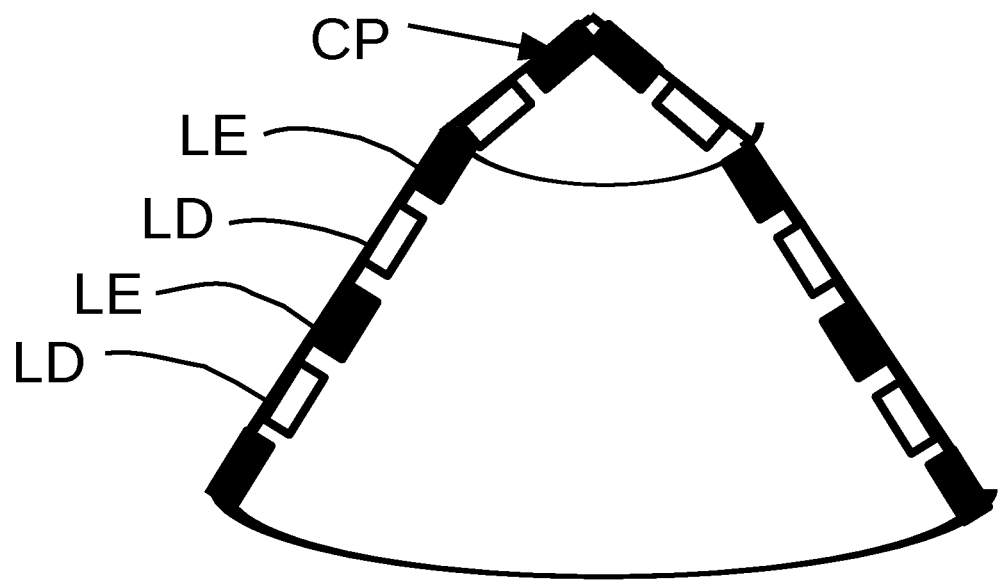

FIG. 10. Variation of cup CP shape: cone's angle change, larger vertex angle.

Figure 11:
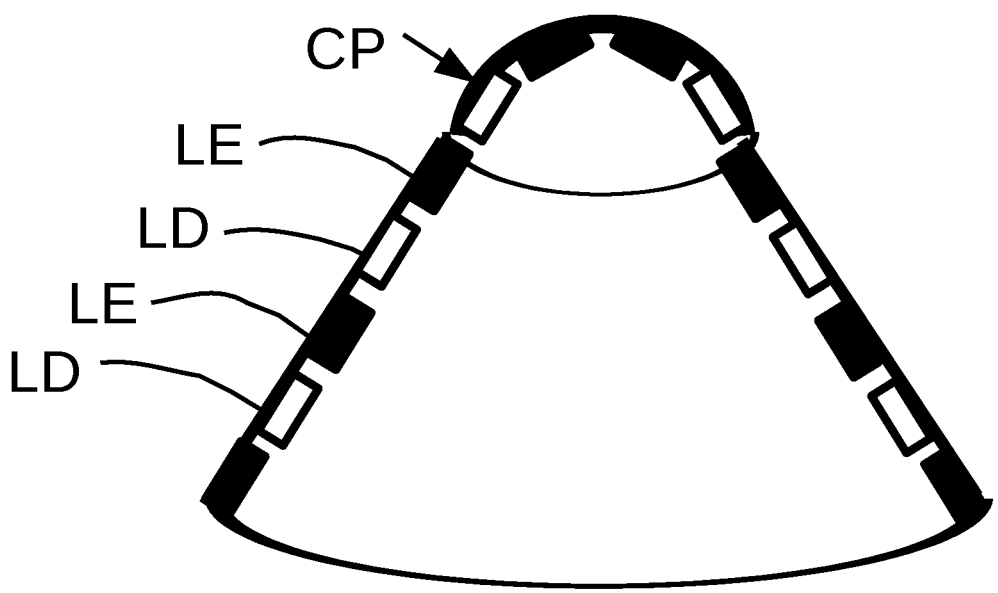

FIG. 11. Variation of cup CP shape: curved upper part

Figure 12:
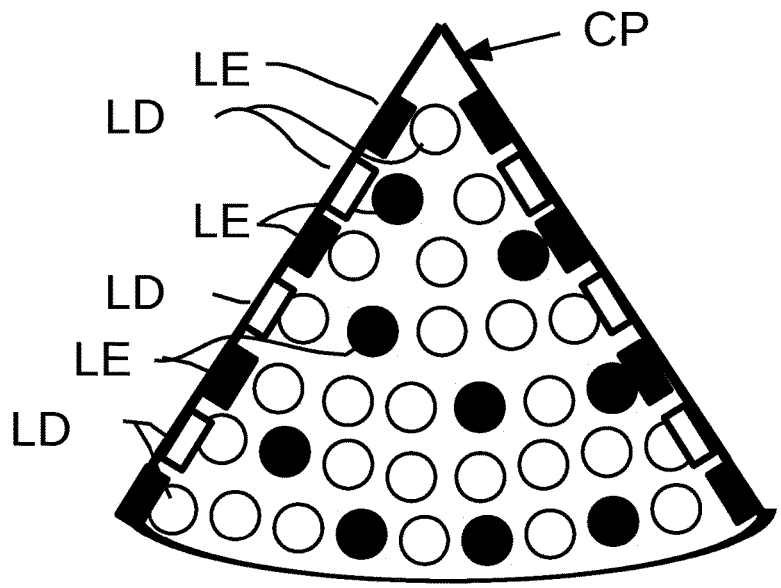

FIG. 12. Cup (CP) of our invention with light emitters (LE, open circles) and light detectors (DET, black circles) in the inner face of the cup of our invention.

Figure 13:
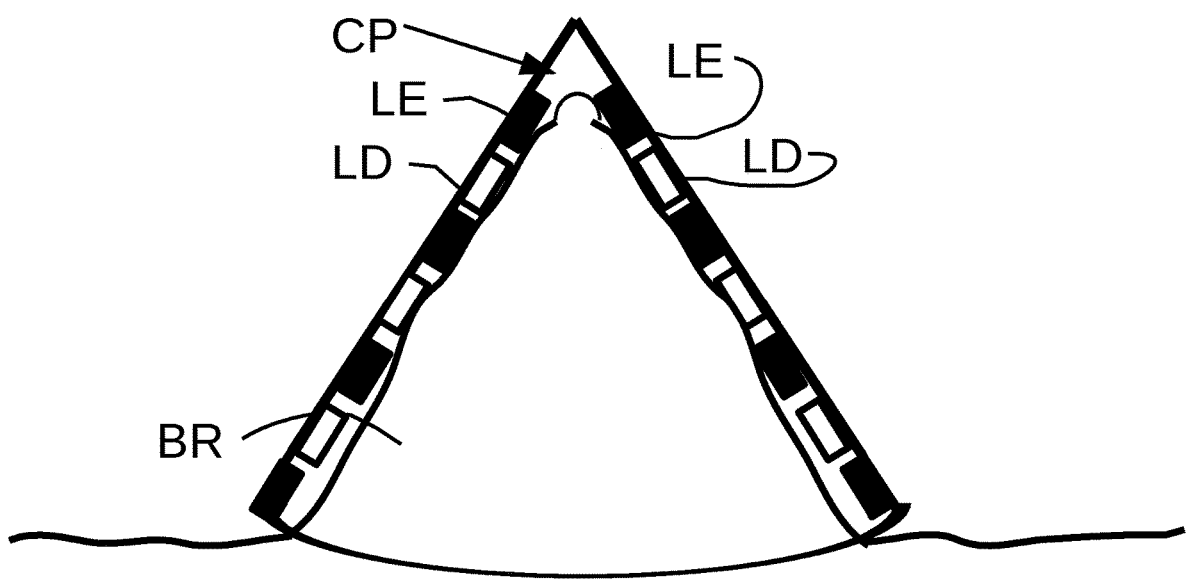

FIG. 13. Cup (CP) of our invention with light emitters (LE) and light detectors (DET) in the inner face of the cup of our invention covering a women's breast (BR).

Figure 14:
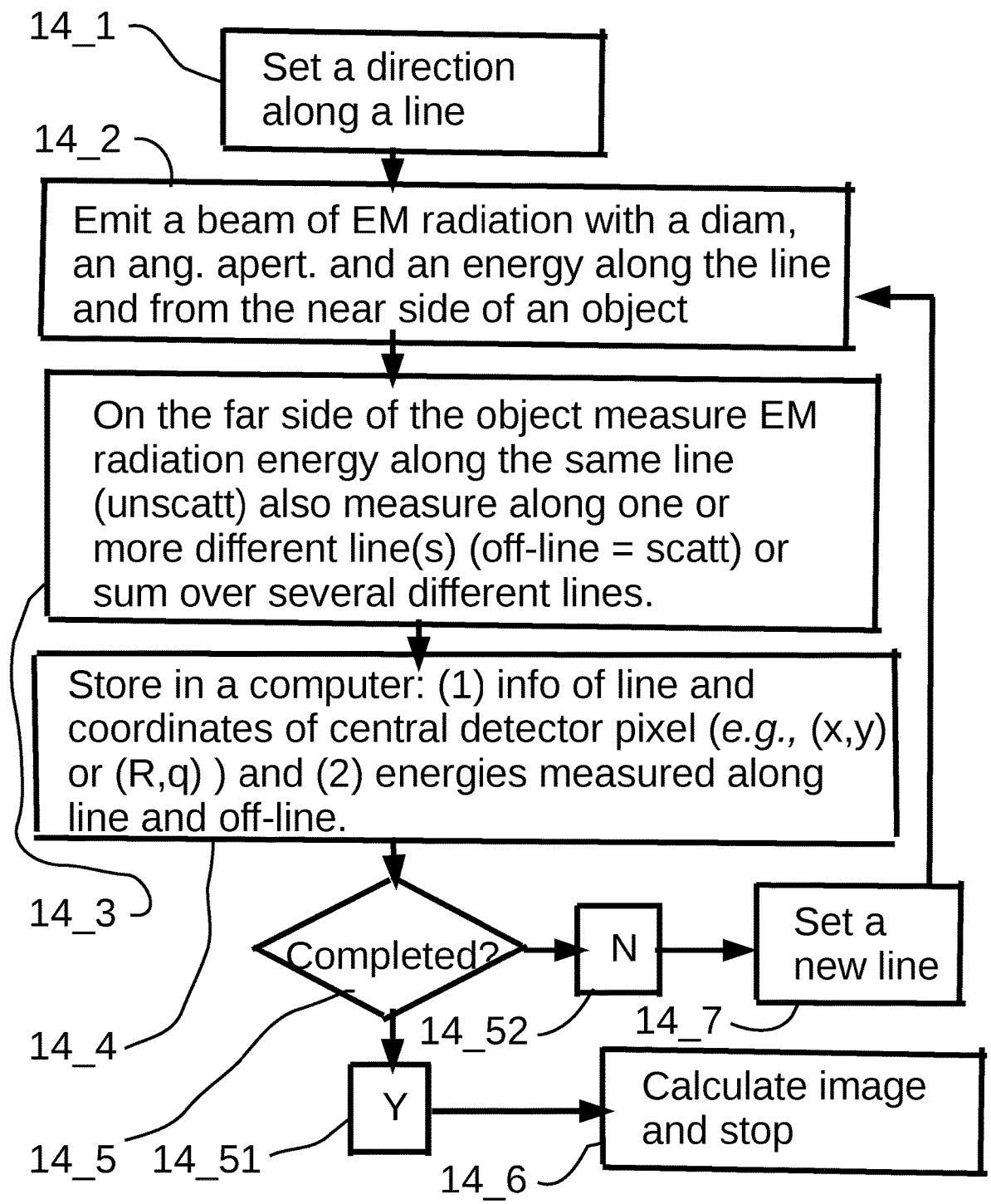

FIG. 14. BlockDiagram shows a block diagram of the image acquisition process

LIST OF REFERENCE NUMERALS

Hd=head object, also Br for breast object.
LP1=liquid (or paste) that fills the gap between the wedge W2 and the object Hd.
n1=index of refraction of medium 1.
n2=index of refraction of medium 2.
BR=brain.
d1, d2, d3=distances from the interface to each scattering point.
HD=Head, one of the possible objects.
LP1=liquid-paste filler.
M1, M2=two medium of propagation. M1 is characterized by T=1 (transmission cross section, or transmission probability), S=0 (scattering cross section, or scattering probability), A=0 (absorption cross section or absorption probability, and M2 is characterized by T=0.01, S=0.985 and A=0.005. This approximately represents an infrared beam propagating in air (M1) and living animal cells (M2), as bones, flesh and blood.
OP1=observation point 1.
SA1, SA2, SA3, SA4=position of scattering events.
SB1=position of scattering event.
SK=skull.
SP1, SP2, SP3=positions of scattering events.
W2=wedge 2, used for refraction index matching
110 or uret=Urethra.
120 or prost=Prostate
130 or blad=Bladder.
140 or rect=Rectum.
150=Anus.
160 or pen=Penis.
310=Finger.
320 or IR-emit=Infrared emitter.
330 or IR-rad=infrared radiation, infrared ray (more correctly, path of infrared radiation)
340 or IR-det=Infrared detector.
350 or tube=Tube with wires and infrared emitter capable of being inserted in the urethra from the penis.
410=Video display for infrared image (or other wavelengths).
420=Medical practitioner obtaining image for clinical examination.
430=Patient in surgical table.
440=Keyboard and integrated mouse.
450=Computer.
510=Smaller pixels near the center of infrared detector IR-det (340).
520=Larger pixels away from the center of infrared detector IR-det (340).
DS=distal side
PS=proximal side
RG=blocking ridges to prevent IR directed from any particular unit to reach an adjoining unit due to scattering and changing direction by a large enough angle.
spe=proximal side, external surface
spi=proximal side, internal surface
sde=distal side, external surface
sdi=distal side, internal surface
s2=distal side
s1=proximal side
s1$e$=s1 external
s1$i$=s1 internal
s2$e$=s2 external surface
s2$i$=s1 internal surface

INTRODUCTORY DESCRIPTION OF OUR INVENTION

The main embodiment will be disclosed for an application of cancer screening and/or confirmation on female breast cancer, but the same principles do apply for head imaging, for tongue imaging, for image of a finger, or any other animal part that has a path through of a few centimeters (or a few inches) from one side to the other, and also for most of the body of infants.

The inventors ask forgiveness from the readers for stepping back onto perhaps too obvious observations. The observant reader can skip this paragraph if she/he so wishes. When there exists a highly scattering medium between an object that one wants to observe and the observer, as a shower glass or plastic is in the path of the light from a naked person inside taking a shower and someone else in the bathroom, the consequence is that the light emanating from the object is mixed in all directions, which blocks the formation of an image of the observed object. In the case of a shower door the scattering is just enough to hide the details of the body inside, yet not so much scattering as to hide the presence of a person inside the shower compartment, and it is so on purpose. Other types of doors produce more scattering than a typical shower door, so not even the presence of a person on the other side of the door can be perceived. Without the scattering glass, all light that emanates from the observed object, which propagates from any given point on the object surface into a cone with apex at the given point and base at the opening of the iris of the observer, is focused onto a single point on the retina of the observer. This is true for all points on the object: all light emanating from any single point on the surface of the object, after propagating along many directions within a cone delimited by the size of the iris at the base of the cone, is brought to another single point on the surface of the retina at the back of the eye—the set being known as the image. If the observer's optical system (the lenses in her/his eye) is not working properly, then each point on the object is focused on a point ahead of the retina, from which point the light diverges again, impinging on the retina over a circle, instead of on a point, which causes image blur. This is easy to correct with a lens kept by a frame in front of the eye, or with a contact lens. If, on the other hand, the light emanating from the object is scattered on all directions along its trajectory to the observer, perhaps by a "bathroom glass door", then the problem is more difficult to solve—indeed, a lens or a mirror are incapable to solve this case, no lens and no mirror can make an image of an object behind a scattering surface. But a solution exists for this case of scattering, which is to illuminate the object one point at a time. When a particular point (or pixel, so to say) is red, then all the even illumination beyond the "bathroom glass door" is red too, because red is the only thing that is reflected from a red point. Moving the illuminating light point to another position, perhaps beyond the "bathroom glass door" it is all still red, perhaps because there is a large red region on the object. Moving again the illuminating light point to still another position, etc., etc., you get the picture (no pun intended): point-by-point the information is gathered about the object: where it is red, where it is green, where it is bright, where it is dark, etc., etc. This is all a computer needs to display the image of the object behind the "bathroom glass door"!

The invention is a device that takes advantage of the increased transmission of infrared photons through animal cells, when compared with visible photons, and also of the large difference of transmission and scattering by blood, when compared with most of other animal cells. The earlier (increased transmission for infrared) is crucial because there are not enough photons in the visible spectrum that propagate through even 1 cm (0.5 in) of human tissue, so the visible part of the electromagnetic spectrum is useless for imaging of inside of the human body, while the latter (the unequal transmission and scattering between blood and other cells) is useful because cancer always increase blood supply to bring nutrients for the growing cancerous mass, or, in other words: more blood per unit volume is an indication of possible cancer. To make our point here, it would be possible to state that our invention is not a cancer screening device, but rather it is a device that detects an increase in blood supply in a particular volume in the body, which is, in turn, an indicator of cancer This description of the main embodiment of our cleaver and beautiful invention is for the particular case of the female breast cancer, but the reader will understand that the same description applies to the case of other organs, as the stomach, the esophagus, the stomach, the prostate etc., with trivial modifications that we disclose in this patent application.

This invention relates to the general field of female breast cancer screening, detection, and confirmation of cancers detected by other methods. Currently the other method of screening (detection) are self-examination, where the woman try to detect new lumps inside her breast by pressing with her fingers, or to detect change of shape or color of her breast, or the same exam performed by a medical practitioner, or X-ray mammogram, or ultra-sound image of the breast and even MRI image. Each of these indicate a different aspect of cancer, and each of these have both false positives (a certain fraction of the results say that there is cancer when there is not a cancer) and false negatives (a certain fraction of the results say that there is no cancer when in fact there is a cancer). Because of this, and particularly because of the false positives, once one of these methods indicate the existence of a cancer, another screening method is applied to confirm or to rule out the existence of cancer. This confirmation is important because ultimately cancer must be confirmed by tissue biopsy, which is a painful process in most cases, which the medical community tries to avoid for being painful.

One of the characteristics of cancer is the ability of the growing mass (the growing malignant tumor) to develop blood vessels to support further growth, which allows more cells to appear by mitosis and tissue growth. Blood vessels are needed, because the nutrients can penetrate only little by diffusion from cell-to-cell (about 2 mm), from cells next to the blood supply to other cells away from direct blood contact at the capillary vessels. Not all cells are next to a capillary vessel, but also no cell is too far from a capillary. Capillary growth, in turn, is a natural phenomenon, known as angiogenesis, which is necessary for most animals to survive normal wounds that happen to all animals throughout their lives, which by necessity disrupts blood flow, in some, or many cases, sufficiently to cause enough lack of nutrients to cause the death of some cells, starting the process of gangrene, which would end with the death of the animal. Angiogenesis, which is a normal, natural mechanism, causes new blood vessels to grow, when normal blood supply is disrupted by wounds that cuts blood vessels, resupplying the remaining cells with oxygen and nutrients from newly grown blood vessels. The process is well known, it is controlled by information coded in the genes, which produces proteins and other molecules that can start and control the process. Cancer simply makes use of this available machinery, a machinery encoded in the genes of most animals, if not all animals, and the ability to start angiogenesis is one of the steps that the cancerous mass must control before it become a real cancer. Until the cancerous mass succeeds in detonating angiogenesis it cannot become a malignant mass, because its growth is limited to a small size, which has little impact on the organism. Looking at it from another point of view, a cancer mass that had to stop at 2 mm diameter would not threaten the life of the person. Moreover, this increased blood supply developed by the cancer mass, shows a malformed, messed up growth of vessels, departing from the normal blood vessel distribution. A normal, health blood vessel distribution progresses from large arteries to smaller arteries, then through smaller and smaller vessels until the smallest capillaries, then congregating back through larger and larger vessels to smaller veins then to larger veins on the vein side (blood return). This increased blood supply developed by the cancer mass generally is much different than the normal distribution, with the vessels at a disorganized pattern, usually disorganized in both sizes and direction of flow. The pathologist looks at such characteristics to make a decision about the tissue in his microscope slide. This disorganized blood vessels growth has in turn another consequence for the cancerous mass growth: it is inefficient at supplying nutrients to the cancer cells, because the blood flow is not uniform flowing from the source (left heart ventricle via the arteries, moving "forward" in a sense) to the return (right heart atrium via the veins moving "backward" in a sense), which in turn forces even more blood vessels to supply the nutrients for the cancerous mass, given that this cancerous angiogenesis is inefficient in supplying blood.

Recapitulating, because this is crucial to the invention, it is known that along its path to malignancy, cancer develops angiogenesis on its environment (that is, the ability to grow new blood vessels within the cancer mass). In fact, the ability to change the cancerous environment allowing angiogenesis to occur, or to take place, is one of the steps, controlled by genetic orders, which must be mastered for an incipient cancer to become a life threatening mass, and in fact some of the chemotherapy is exactly drugs to block angiogenesis to occur. This is so because until new blood vessels are brought in, the cancerous mass is limited in size for lack of nutrients. It is know in the medical community that though all cells have the intrinsic capability to start the process of angiogenesis, something, only partly known to the scientific/medical community, must occur to start angiogenesis. Any cancer will stop until the cells that compose the cancerous mass develop this capability, or in more clear words, until the cells that compose the cancerous mass begin triggering the angiogenesis process, which is already part of their genetic code, part of their DNA.

As a consequence of this mechanism of angiogenesis, all cancer masses are extensively irrigated with blood, and like king Midas they overdo, overproduce capillaries and have more blood irrigation than non-cancerous tissues around it. This excessive blood supply is one of the characteristics of cancerous masses. Our amazing invention makes use of the increased blood supply in cancerous masses, as compared with normal tissue around it, and the possibility of detecting blood inside a sea of other types of cells by its infra red signature, that is, its differential infra red absorption and scattering properties, when compared with most other cells in the human body.

As for detection, blood can be detected by the differences in its absorption and scattering of electro-magnetic radiation, particularly in the near infrared. Visible light towards the shorter wavelength side (higher energy photons) is of little use for this, because the absorption of blue-ish visible light is so strong that the process would be difficult, given that so few photons survive the most short path in tissue. Near infrared (NIR) radiation, though, provides enough transmissivity to be usable. Red visible light is also acceptable, but NIR is better due to the transmissivity of NIR being higher than the transmissivity of red visible light. Consequently, our invention recommends infrared radiation, and more specifically, near infrared radiation as the preferred choice. In particular, the preferred wavelength is around 850 nm, which is the wavelength of maximum transmissivity in animal tissues. In the infrared region of interest for us, the decrease in photons along the incident direction is due far more to scattering than to absorption, with a roughly 100 times larger scattering cross section (probability) than absorption cross section (see definition of cross section at the definition section, it means probability, more or less). The wavelength range of usable NIR image in tissues is roughly from 750 nm to 1,000 nm, the best range being between 800 nm to 900 nm. Consequently the inventors recommend the wavelengths between 800 nm to 900 nm for the implementation of the invention. Yet, following the advise of patent lawyers, these guys that specialize in claiming that white is black and black is white, as per readings of the inventors, we need to add here that the invention is not limited to the infrared. In reality red visible light also works, just that usually it is not as good as NIR.

The inventors must warn the readers to go slow though, because the formation of the infrared image is not so simple. In fact, an infra red camera positioned at the point from where to see the image (call it the image side) "sees" no image from the "illumination" with infra red. This is so because very few photons transverse the 5 to 10 cm distance from one side to the other of a female breast with no scattering event. The photons that arrive at the image side are akin to the photons that emerge at the outside of the glass (or plastic) that closes the shower stall: one can kind of see a body contour inside, but one cannot see much more, and in the case of infrared propagation through the female breast the "image" is more blurred than the image of a person inside a bath stall. So, given that the infrared photon distribution on the distal side of the breast, along the path of propagation, at the image side, is even more smeared than the visible photons carrying the image of a person inside a shower stall, the "image" must be coaxed from that almost even "light" distribution. Something must be done to retrieve that evened up photon distribution. Something must be done to extract the image from an even photon distribution. This something, the method to extract the image, is described in the amazing U.S. Pat. No. 5,590,169, of one of the inventors here (from now on patent '169). This current patent application is a variation and an addition to the device to obtain the infrared photon distribution from which to extract the image as described in this '169 patent. We now proceed with a simplified explanation of the method to extract an image of the female breast from the almost even photon distribution at the image side.

As a preview to what will be explained in the section "operation of the invention", it is possible to lift an image out of the smeared photon distribution at the image plane using the knowledge of the photon incidence path. For this, the incident photon is aimed along a certain direction (dir_1) then the detector at the image plane measures two quantities: the energy directly along the incidence direction (dir_1) and either the sum of all energies around the incidence direction or else part of this sum. The former (the energy along the incidence direction dir_1) forms a pixel (or a point in the image) of the object, it being the measurement of the beam that was transmitted along the incidence direction, which is what we call "transmitted beam", so this pixel is a pixel of the transmitted image. The latter (the energy scattered around the incident direction dir_1 and, at the detector plane, around what we call "central detector") forms another pixel (or a point in the image) of the object, it being the measurement of the scattering cross section of the cells along the incident infrared beam, so this pixel is a pixel of the scattered image. The more blood there is along the particular incident direction, the more absorption and more scattering there is along that direction, both of which subtract photons from the beam, and therefore the smaller is the energy remaining along the incident direction, which means that the transmitted image is a negative image of the blood volume along the incident beam line, or along that direction through the object: more blood=less photons. But the scattered pixel is the opposite: the more blood along the incident direction the larger is the scattering and therefore more photons (infrared radiation) around the central detector (around dir_1). It is worth to emphasize here that the scattered photons are perfectly capable of forming an image by themselves—as long as the direction of propagation of the incident photons (or infrared beam) is known.

It is our experience that so many people get perplexed that the scattered photons (or scattered infrared radiation) does carry all the information to make an image of a completely blurred object inside a scattering medium, that we repeat this last statement about the scattered radiation. The numerical value of the energy measured by all detectors or just some of them or just one of them, around the incidence direction (dir_1) contains enough information to retrieve an image of the object—and a fairly good image, for that matter! The inventor clearly saw this with his mind, people around would not believe, the inventor then constructed a device to do it, and the images were actually better than the inventor saw in his mind—which, in retrospect should not have been surprising, as I now see. This image retrieved using the scattered radiation is the reverse of the situation of the energy measured by the detector on the point directly on the line of path of the incident photons (dir_1). While the infrared energy along the direction of the incident beam decreases with more blood on the path, the infrared energy around the direction of the incident beam increases with more blood on the path—so, it is a negative image. The more blood that there is along the direction or line dir_1, the more scattering that there occurs, so the larger is the measurement on each of the detectors surrounding the detector along the incidence line and, a fortiori, the sum of some of them or all of them. The total energy measured by any one or several of these surrounding detectors is a measurement of what we call scattered image, because it originates from photons that have suffered one or several scattering events within the object. Note now that though the single small detector along the incident direction measures one point of the transmitted image, the scattered image is "lifted" from either any detector on the surroundings of the detector along the incident direction of a few of them, or an integrated (a mathematical term meaning summed) or combined or summed of the measured values of many detectors around the "central" detector that measures the transmitted image. Any single detector is capable of gathering the data for the scattered image, but, as the reader will see with a little reflection, it is better to integrate (that is, to sum) the detector around the "transmitted" detector for a better statistics. The single point of measurement along the incident direction is an also single point for the transmitted image coincident with the position of the measurement point, while the measurement of the energy around the same particular point is also a single point for the scattered image, but for the scattered image, this point is not at the measured position, but at the point on the image plane which is pierced by the incident direction, which is the same point of the transmitted image. These images, both what we call "transmitted image" and "scattered image" are projection images, akin to an X-ray image, images devoid of depth, as the typical X-ray picture is devoid of depth information.

Once the reader understands the above description, it is just a small step to understand that a complete image of the object is retrieved from a scanning of the object which goes as such: stop the infrared beam at some direction, such that the infrared beam pierces the object, measure the energy on the detector along the incident direction (dir_1), then measure the energy on one, some (or all) of the adjoining detectors around the detector mentioned above, the sum of which is a measurement that indicates the brightness of the scattered image at the same direction where the incident beam pierces the object. Then move the incident beam to a new position, measure the transmitted intensity and the scattered intensity, which are another point each on the transmitted image and on the scattered image, then move the beam again, measure again, etc., etc.

It is a useful curiosity to remark here that the red color that one sees when looking at a thin piece of tissue that is back illuminated by a strong white light, as the sun, for example, back illuminating the ear lobe or the skin between the base of the fingers, is a consequence of the above mentioned difference in transmissivity, which starts working on the end of the red spectrum already and the infrared just transmits more than the visible red. When one of the inventors (SLPM) was a child he was fascinated by the red light seen in these circumstances, imagining then that he was seeing his blood; but he was actually not seeing his own blood, he was wrong, the red he saw was the remaining light from the white light entering the ear lobe, or the thin flesh between the fingers, only the red survived on the distal side, all the other colors having been absorbed, this being why our invention works well in the infrared, though it works in the deep red too, just not as well. So infrared lends itself more to producing an image of the blood within the flesh, e.g., in a female breast. Also, it is a continuous red, without spacial features, because this red that is transmitted through a thin human tissue slice (ear lobe, flesh between the fingers, etc.) is transmitted after many episodes of scattering, since the scattering cross section (probability of scattering) for most tissues part of the human body at the near infra red is approximately one hundred times (100) larger than the absorption cross section, so the ordinary image is spread out, so to say, instead of blocked. For the other colors though, particularly yellow and beyond, the absorption is larger, and virtually no photon survives the propagation of as little as a few millimeters of body tissue, let alone even an oriental breast, let alone a German one. An illuminating point source at the distal side (back side) appears as a large circle on the proximal side (front), after many scattering episodes—just make a drawing of it! Repeating it, because this is crucial for the understanding of our invention, for the infrared transmission in most animal cells, the image is destroyed by scattering, not by absorption. Again, because the point is important for the understanding of the invention, we make here an analogy with the frosted glass that covers many shower stalls. The details of image of the naked person inside the stall is washed out due to multiple scattering, as the light propagate through the frosted glass. The frosted glass separating the shower stall from the rest of the bathroom prevents any detailed image to be seen, while still transmitting light. This analogy with the frosted glass enclosing the shower stall is only partial, though, because the intention in the shower stall is to wash away the details of the body inside, due to the christian fear and horror of nudity, yet still allowing people to see that there is someone taking a shower there, while the infra red case of transmission through tissue is an extreme case of the frosty shower stall, one with a thicker glass that does not allow the viewer to discern a body inside the stall, but only a totally even light distribution. Of course that if our eyes were sensitive to infrared radiation we would see not a red but an infrared transmission through the flesh, the infrared being the dominant "color" because of its much larger transmissivity when compared with even the red. Luck has it too, that blood has a substantially higher absorption and scattering cross section (or probability, see definition if you are not a physicist) when compared to other cells in the body, so it happens that blood can be detected by its higher absorption and higher scattering within a medium of other cells. Using the terminology of physics, blood has sufficient differences in its infrared absorption and scattering cross sections to detect blood inside a sea or other non-blood cells. The differential scattering cross section of blood, when compared with most other cells, is true for both forward scattering and back scattering as well—which is another fact on which our invention is based.

Another interesting analogy and comparison to help the reader to understand the invention is the X-ray. I am now assuming that the reader have seen at least once an X-ray image, say, of a bone. The bone appears lighter, when compared with the flesh around it, on the (black-and-white) picture, while the flesh appears darker, when compared with the bone. This is so because the bone absorbs more X-rays (photons on the X-ray region), so there are less of it beyond the bone and consequently the bone appears lighter. The image is due to the difference between the absorption of X-rays by bone and by flesh. There would be no image if bone and flesh absorbed X-rays the same way! Likewise, to make an image of blood in an organ, it is necessary that blood has a difference in either the absorption cross section or the scattering cross section (probability of absorption and scattering in physics language), when compared with flesh and other tissues. As it happens, there is a measurable difference in both transmission and scattering cross sections that either is enough to make an image of blood inside flesh in the human body.

Another interesting use of this feature of light, which is an old medical practice, is the detection of breast cancer using what became known in the medical field as transillumination. This method is now falling in disuse because the pharma business and the big corporations cannot make money from it, but it was used more widely then today until WW II. The evidence for its effectiveness is mixed because there are reports from practicing physicians that transillumination worked, though not perfectly, and reports commissioned by companies as GE, etc. that manufactured X-ray mammogram devices, which concluded that transillumination was a ruse. Transillumination is a medical procedure that is not in line with the medicine practiced in a capitalist nation as the United States so it went the way of the dodo. It consisted in back illuminating the breast of women, then observing with the naked eye the light pattern that is transmitted. The illumination was with deep red light, with both the patient and the physician in a dark room. The physician needed to stay in the dark for enough time for his eyes to get adapted to night vision (for her pupils to open), which was necessary due to the small number of transmitted photons. This technique is still used by physicians serving poorer communities, with less access to high-tech options, as mammography. Also, some high-tech, modern variations of it are being studied and developed in research facilities in universities in Russia, China, Europe, Korea, Japan, and even USA, but it is less common in USA because the method cannot produce as much money for the big companies as the X-ray mammography and MRI versions do. The high tech variations of transillumination are based in either time-of-flight that selects the transmitted photons on the shorter direct path (no scattering) along the incident direction (picosecond pulse), which by necessity arrive earlier on the observational side due to its shorter path, and an interference method, which is based on the phase differences between scattered and transmitted photons. The former is also known in the field as time domain method and the latter as frequency domain method. Our invention is an alternative method to these two, not the time domain method, I prefer to call it time-of-flight, which necessitates picosecond pulses from an expensive laser, not interference, which necessitates a bean with excellent transverse coherence, also expensive, but a method that works with an inexpensive $2 infrared diode laser plus some $10 worth of optical parts, then an arduino duemille or equivalent microprocessor, and this is all. The inventors expect that the American big companies will oppose our invention.

Rephrasing it all again, blood has different absorption and scattering cross-sections (to use the physics terminology, which in common parlance is said probability) in the near infrared radiation, when compared to other types of cells, as muscles, etc. Stating it differently still, blood absorbs more near infrared radiation than other cells, as muscle cells, etc., even bones, and blood also scatters infrared photons more as well, both forward and backward. This, in turn, may be used to detect extra blood in breasts, which, in turn, is a marker for breast cancer that has already mastered the angiogenesis (that has already passed this cancer stage) because the blood circulation through the cancer mass is larger, and enough to be detected. In other words, our invention is a device and a method to make an image of increased blood supply within a cancerous volume using the larger absorption and scattering cross section of blood to the near infra red radiation when compared with any and all other human tissues.

For this detection of the infrared radiation that has propagated through a breast tissue that is under investigation it is preferable to use either (1) a clear path through the breast, as from side to side, or from the top to the bottom, or at some slanted angle, or along some smaller path within it, or (2) a detector at the same supporting base as the emitter, used for back scattering. This latter, second option, suffers from the drawback that most breast cancers are deeper than 2-3 cm from the surface, in which case the back scattering is marginal for detection and imaging. For the case (1) it is also preferable to measure both the transmission and the scattering, and from these, the absorption, which is the original energy minus the transmitted and scattered energy. This is described in the sequel.

Now it is time to finally go into our wonderful invention. But before, and in preparation for this, I want to share with the reader the history of a demo unit that the inventors built. This demonstration was built because my colleague Hanguo doubted it worked and we made a bet. As a consequence of our bet, Gunnar Skulason joined me and we build a demo, it worked, Hanguo saw it, and we gained a Chinese dinner.

Figure FIG. 14 is a block diagram of the principle of operation of the invention. Step 1, indicated by 14_1 is to set a direction along a line. This is followed by step 2, marked as step 14_2 in the block diagram, which is to emit a beam of EM radiation with a diameter (diam), an angular aperture (ang. apert.) and an energy along the line and from the near side of an object. The next step, which is step 3, indicated by numeral 14_3, is, on the far side of the object measure EM radiation energy along the same line (unscatt) also measure along one or more different line(s) (off-line=scatt) or sum over several different lines. This step is then followed by step 4, which is labeled 15_4. which is to store in a computer: (1) info of line and coordinates of central detector pixel (e.g., (x,y) or (R,q) and (2) energies measured along line and off-line. This is, in turn followed by step 5, labeled as 14_5, which is a question: Completed?. The reply to this question can only be Yes or No. The former case, yes, is labeled as box 14_51, which is Y. The only step after falling in step 14_51 can be step 14_6, which is to calculate image and stop. On the other hand, question 14_5 could be replied on the negative N, which is box labeled 14_52, which is necessarily followed by step 14_7, which is set up a new line, which returns the process to step 2, labeled 15_2. The principle of operation, according to a computer program runs these steps until it end at step 14_6.

The crux of the matter for our device to work is to force normal (perpendicular) "light" incidence on the object, and exit from the object as well. This normal incidence is the crux of the matter here: without a known angle of incidence, the direction of the radiation emerging on the other side of the object (the breast, the box, etc.), which obeys Snell's law, is also unknown, which then causes that the propagation direction of the photons inside the breast is unknown, which then means that the incidence angle for the exiting surface is "even more" unknown, and then the poor last refraction is totally unknown and no image can be made, nothing, no more, kaput, finito! This is so because the image CAN be reconstructed as long as the trajectory of the incident beam in known inside the object, required to lift the scattered image. If, besides this trajectory inside the object, the observer also knows the trajectory of the beam after it emerges out at the exit surface, then a second, independent image can also be lifted, the image that I call "transmitted image". So, we are then faced with the problem of forcing the radiation beam (the laser beam, the infrared beam, etc.) to impinge on the breast at normal incidence, all the while that the breast keeps curving, from its base, at the chest, to it apex, at the breast's nip. At first this seems to be an impossible problem, with no solution, but the solution is actually amazingly simple. This is what we proceed to describe now, ant the solution to this problem is our invention—so beautiful invention it is!

We will here use FIGS. 2 and 3. Both FIGS. 2 and 3 are simplified drawings of the wonderful breast cup of our invention. Both these drawings show light emitters and light detectors only on the sides of the conical breast cup of our invention, omitting both light emitters and light detectors on the surface facing the viewer and on the (invisible) surface behind the visible side of the breast cup of our invention. The reader must keep in mind that there are both light emitters and light detectors on all the surface of the approximately conical breast cup of our invention. The shape of what we are here loosely calling "conical breast cup of our invention" is such that it fits on the patient's breast, including a patient molded cup designed to more perfectly follow the contour of the breast of the patient. Another detail that needs to be present in the mind of the reader is that the breast shown at FIG. 3 is depicted the way it is, only for information. In reality the light emitters and light detectors are small protuberances on the inside of the breast cup AND the design is such that the soft breast tissue accommodates itself along the inner surface of the breast cup leaving NO space between the breast surface and both the light emitters and light detectors. This close fitting, this physical touching of the patient's breast to the light emitters (LE) and light detectors (LD) at the inner surface of the cup of our invention is an important feature, because it forestall the change of incident light (incident infrared "light") caused by Snell's law. Variations on the position and direction of the light emitters LE and light detectors LD are possible as long as there is always one light detector well aligned with each light emitter LE, which is capable of measuring the value of the radiation (infrared light) that has suffered no scattering along that particular direction between the light emitter LE and light detector LD. The light that suffered no scattering between a light emitter LE and a light detector LD is called here "transmitted light", and the reader is again warned that this use of the word is not the usual, defined way in optics, but it is a personal use of the expression.

FIG. 2 shows the cleaver breast cup of our invention by itself, not inserted over a breast, while FIG. 3 shows the same cup inserted over a breast. The reader can see alternating light detectors (LD) and light emitters (LE) facing the inside of the breast cup, that is, facing the female breast that is inserted inside the breast cup of our invention. Consequently both the light detectors LD and the light emitters LE face the female breast when in use. Figure FIG. 2 also shows two paths of propagation of two laser beams, or, to use the ordinary language, two light "rays". The diameter of each laser beam may be of the order of 1 mm, the divergence may be of the order of 1 mrd (milli radian), and the power may be from 1 mW to 1 W, but these values are not mandatory for the working of our invention, wider and/or narrower laser beams, larger and/or smaller beam divergences, and smaller and larger power being also compatible with the method that we will describe below. Though this caveat about the laser beam diameter and divergence and laser power is unnecessary to anyone with technical knowledge, we are aware of the lawyers' propensity to twist the intended meaning of words, so we reluctantly added this caveat above, lest any lawyer in the future try to knock down our beautiful patent with their absurdities.

Figure FIG. 3 shows the same breast cup of our invention with a female breast inside the breast cup. As stated above, and we repeat here because of the damn lawyers, both the light emitters LE and the light detectors LD are much smaller than their size on this FIGS. 2 and 3, that is, they are much smaller than the relative size when compared with the size of the female breast and the breast cup shown, the larger size of the light emitters LE and light detectors LD being only to clearly show both LE and LD, including their relative position with respect to each other. Also, again as stated above, when the female breast is inserted inside the breast cup of our invention, given that the female breast is soft tissue, it normally accommodates itself in such a way as to leave no space between the breast's skin and the surface of both light emitters LE and light detectors LD. For this to occur, the breast cup of our invention needs to be of the same size, perhaps ever so slightly smaller, than the female breast that it covers, and therefore a clinical setting should have a number of breast cups of different sizes, to be chosen to accommodate any particular patient. Though the inventors suggest the use of a breast cup that is just slightly smaller than the breast under examination, the actual size of the breast cup of our invention depends on the clinical experience and other consideration of the medical practitioner. The reason for this restriction of close fitting between the female breast and both the light emitter LE and the light detector LD is that if there exists an air layer between the female breast ant either the light emitter LE or the light detector LD, then refraction of the light beam as it enters or exits the breast would change the direction of propagation of the light beam, which is not allowed to occur according to the method of our invention. In other words, the method of our invention requires that the beam penetrates the female breast with a perpendicular incidence (that is, the angle of incidence is zero degrees, the angle here being defined as the angle with the normal line (perpendicular line), as per the convention adopted in optics). This is so because normal incidence (perpendicular incidence) is the only angle of incidence which does not change the direction of propagation of the laser beam, so normal incidence is necessary to keep the laser beam on a known path, which is necessary for the method of our invention, as the reader will see below.

Some fraction of the emitted radiation propagates inside the breast BR along the initial direction (along the original direction defined by the small angular divergence photon beam) and mostly of the emitted radiation suffers multiple scattering for the case of infra red radiation, easily propagating through 5 to 10 cm (2" to 4") distance from the emitter LE to the detector LD. The photons that reach the detector without suffering a scattering event (and without being absorbed too, of course), form what we define as the transmitted beam. This transmitted beam can be used to form what we call transmitted image. Along a particular direction of propagation the transmitted beam determines one point (one pixel) on an image, on the transmitted image. In other words, the transmitted image is a projection, similar to an X-ray image is a projection as well. Repeating it in different words, it is understood here that the image we are referring to is a 2-D image of a 3-D object (a female breast). It forms an image because it contains the information of the opacity (defined as the sum of the absorption and the scattering cross sections) of the object along the direction of propagation defined by the emitting source (which, as the reader remembers, is a thin photon beam, in practice approximately a 1 mm diameter diameter beam, which we call a line). This beam contains less photons if there is more blood along its path, because blood has both a larger absorption cross section and a larger scattering cross section as well, when compared with any other type of cell in the organism, including the bone, so less photons survive the trip and less arrive at the LD. It is counterintuitive that the absorption and scattering cross section of blood is larger than the equivalent quantities for bone, but this is counterintuitive only because we reason with visible light and we never see infrared, and the absorption and scattering cross-section for human tissues are not the same as for infrared radiation. Because there is less photons (darker) when there is more blood, it follows that the transmitted image is a negative image of the blood supply, using the term negative image in the same way as used in the good 'ol days of 35 mm photography. As the photon beam scans the object (the part of the breast that lies between the emitter and the detector), there will occur "darker" points that corresponds to larger absorptions or larger scattering along that particular line. These points may indicate larger blood supply along that particular direction, something that has to be later interpreted according to the image, as part of the training of a medical professional, similar to the training of an X-ray trained physician. Repeating the above, the infrared beam scans the object (the breast), emitting photons that penetrate the object (the breast) along a sequence of lines. The energy of light distribution along the direction of each line is a measurement of the opacity of the object (the breast) along each line. The controlling computer knows the position and direction of the infrared emitter at each new line, which is matched with the intensity of infra red radiation on the pixelized detector at the detecting plane. The detector that is directly along the line of emission receives the infrared photons that corresponds to the transmitted beam and they form, point-by-point, as the emitting beam moves on an x-y pattern scanning the object (the breast), a pixelized image of the object (the breast). This image is what we call transmitted image because it is made with the transmitted photons, and the transmitted image is a negative image because more blood along the propagation line means less photons at the detector along that line.

Recapitulating, an infrared light beam (as an infrared laser beam or similar) scans the object with the light source LE on the near side of the object (the breast in the case of the main embodiment). At each position of the beam, it determines a line through the object, which propagates from the near side to the distal side of the object. On the distal side of the object the light beam, which originated as a small diameter, small divergence beam (say, R=1 mm, div=1 mrad), typically is a wide beam, due to the scattering through the object, with a larger beam divergence than the initial beam divergence. The light energy that is measured on the distal side of the object along the initial beam direction, is the measurement of the light energy that suffered no scattering and was not absorbed. The more blood there is along any particular line through the object, the less is the light energy that is measured on the distal side of the object along the initial beam direction, because blood both absorbs more and scatters more infrared radiation then other body cells. Therefore, as a controlling computer causes the infrared light beam to scan the object, a series of numbers is generated, each number being a measurement of the amount of light along each of the lines

DETAILED DESCRIPTION

Referring to FIGS. 4 and 5, our amazing invention consists of a supporting structure (SS), a controlling computer (Comp), a software running on the controlling computer Comp, optional motors (MOT) to move light sources (LE) and light detectors (LD), optional motors to move the object, and the wires to connect the computer Comp to the light sources LE and light detectors LD and motors MOT and everything to the electrical power sources. The supporting structure SS should have the approximate same shape as the object OBJ of which the invention is to make an image, with some electromagnetic radiation, preferably, but not necessarily only, with infrared radiation. The light sources LE (preferably infrared "light") and light detectors LD are mounted preferentially on the inside of the supporting structure SS, as shown at FIGS. 4, 5 and other figures, but other mountings are possible as well, as described below. The supporting structure SS is made in such a way that it covers the object OBJ with the light emitters LE and light detectors LD tightly compressed against the object OBJ. This requirement of tight fitting between light emitters LE, light detectors LD and the object OBJ is necessary for the radiation beam LB to hit the surface of the object OBJ at normal incidence angles (normal=perpendicular), which, in turn, is necessary for the direction of the light beam LB to be known inside the object, which is a necessary condition for our method to work. This requirement of tight fitting is to prevent air gaps between the light emitters LE, the light detectors LD and the object OBJ, because any air gaps would cause a deviation of the light beam LB from its original propagation direction, which must be known for the method and the device to work. The new direction of the light beam LB could always be calculated using Snell's law, but the incident angle would, in general not be known, which means that Snell's law would be useless to calculate the refracted direction of the light beam LB.

The preferred embodiment of out invention is for breast cancer, so the supporting structure SS has a shape compatible to fit a female breast, which we call a breast cup (CP). The preferred embodiment has all the other features named above, as a controlling computer (Comp), a software running on the controlling computer Comp, optional motors (MOT) to move light sources (LE) and light detectors (LD), optional motors to move the object, and the wires to connect the computer Comp to the light sources LE and light detectors LD and motors MOT and everything to the electrical power sources. For the preferred embodiment, the light sources LE and light detectors LD are mounted preferentially on the inside of the breast cup CP, as shown at FIGS. 2, 3 and other figures, but other mountings are possible as well, as described below.

The preferred embodiment of our invention, which is designed for breast cancer detection is shown in FIGS. 2 and 3. The main physical part of my invention is a breast cup (CP) of approximately conical shape, as shown on 2 and 3 and other figures, which serves as a supporting structures for a plurality of light emitters (LE), and light detectors (LD), as shown at FIGS. 2 and 3. For clinical use, several breast cups (CP) should be available, to fit the breast's size of most possible female patients, much like bras are manufactured of different cup sizes. The light emitters LE are preferably laser emitters, as a laser diode, but this is not a limitation on our invention, other sources of light being also possible, lasers being here used as an example thereof (to use the funny, proto-English lawyer's language . . . :)). Mounted on the inside of the breast cup CP of our invention is a number of light emitters, which, in the main embodiment of our invention, are infrared laser emitters IR-emit (LE or 320) and infrared detectors IR-det (LD). Both of these, LE and LD, are located on the inner surface of the breast cup of our invention, preferably aligned as shown in these figures but other positions and orientations are also possible, some of which we discuss here in this patent disclosure but other variations being also possible, as it is obvious to persons familiar with the subject ("familiar with the art", as the lawyers say it in proto English . . . ). The laser IR emitter LE is capable of emitting a beam of infrared radiation IR-rad (330) with the characteristics as follows. The infrared emitter LE (IR-emit or 320) preferably emits infrared radiation IR in a small diameter beam IR-rad (330) with an also small angular divergence. Preferably, but not necessarily, IR radiation emitter IR-emit is a laser type emitter which has typical diameter of 1 mm FWHM (full width half maximum, a common descriptor used in optics) at the exit of the emitting source, and typical angular divergence of 1 mrad. The power of the light emitter LE is typically between 10 mW and 1 W, but this is not an exclusive range, less powerful light emitters LE and more powerful light emitters LE are possible, as it is obvious to persons familiar with the subject.

One important variation of light detector LD is the addition of a collimator CL, shown in FIGS. 6 and 7. The addition of collimator CL forestalls the detection of any photon that is not traveling along the particular desirable trajectory, which may be, for example, the trajectory of the illuminating beam LE. The walls of the collimator CL may be of such a material that it absorbs the radiation of interest (say, IR), which may include a surface roughness as well, to add to the absorption capability of the walls of the collimator CL. For example, if the radiation beam were visible light, any, from red to violet, the internal walls of the collimator CL would be black for the eye of a human animal—after all, this is the meaning of black: no reflection! . . . . The addition of roughness increases the absorption by the wall, because the incidence angle is smaller at many points, when compared with the incidence angle for a smooth surface, which angle can be close to 90 degrees, or grazing incidence, which, by Fresnell's equations, causes a larger reflection, as any person familiar with the field recognizes.

In use, for the preferred embodiment, referring to FIGS. 2 and 3, the supporting cup structure (CP) is fitted with a plurality of light emitters LE (preferably but not necessarily infrared IR emitters) and a plurality of light detectors LD (IR detectors), which are aligned to each other: LE1 aligned with LD1, LE2 aligned with LD2, . . . . , LEi aligned with LDi, etc., Moreover for the preferred embodiment one and one only light emitter LE emits radiation (IR radiation for the preferred embodiment), at any time ti. This point is important for the operation of our invention, so we ask the reader to pause, read this again and think about it. The importance of this single LE light emission at any time is because our invention requires that the computer knows the radiation propagation path inside the object for all the measurements, which is achieved with 1) one "light" beam at a time, and 2) normal (perpendicular) incidence onto the object OBJ, to guarantee no diffraction at the interface from the light emitter LE to the object OBJ. In this working mode, there is one and only one light detector LDi aligned with the particular light emitter LEi that is emitting at any particular time ti. In this situation, LDi measures the radiation intensity ("light" intensity or IR intensity) that was emitted by the light emitter LEi aligned with it, which is the radiation intensity that we personally call "transmitted radiation", which mean, for us here, the radiation intensity that propagated along the initial direction without suffering neither a scattering event nor an absorption event. This is the value of the transmitted pixel Ti (our name, not standard name), which is one point (or pixel) on the transmitted image of the object (the breast). This point on the image of the object OBJ is a projected image of the object OBJ, much similar to an X-ray image, which is also a projected image to the object onto the X-ray film. Similarly, any of the other nearby detectors, or off-axis "light" detectors, say light detector LDi+1 or LDi−1, etc., being NOT aligned with the emitter LEi, measure the radiation intensity that changed direction, that is, the radiation intensity that suffered scattering along the initial propagation direction, being now propagating along a different direction, towards light detector LDi+1, Ldi−1, etc. These light detectors LDi+1, LDi−1, etc. measure the intensity of the scattered radiation along the direction of LEi (because LDi+1, LDi−1, etc. are off-axis with respect to the propagating initial "light" beam LEi), and any of these, or an average of them, are a measure of the scattering radiation energy along the direction LEi, and are the value of the scattered pixel Si, which is one point (or pixel) on the scattered image of the object (the breast). As a note for the nay-sayers, of course that radiation that is measured by any off-axis light detector LDi+1, Ldi−1, etc. may have suffered multiple scattering events, but it still has suffered for sure an scattering event out of the initial direction of the propagating initial "light" beam LEi.

Our invention also discloses light detectors LD (not shown) that are not aligned with any light emitter LE. These light detectors LE that are not aligned with any light emitter LE are preferentially designed to measure "light" within a larger acceptance angle than the light detectors LD that are aligned with light emitters LE. The latter, light detectors LD aligned with light emitters LE may have, and preferentially have, some sort of collimator CL (e.g. FIG. 7). Collimators CL have the function of preventing radiation from any direction other than the initial propagating direction to be measured as radiation that suffered no scattering (which we call transmitted radiation).

In clinical use the medical practitioner 420 locates the appropriate breast cup CP of our invention that fits the patient 430 under examination, then positions the breast cup CP of our invention over the breast of the female patient 430. Cup CP contains also two wires (not shown) to bring electrical power to infrared emitting device IR-emit (LE or 320), and other wires for data transmission to the controlling computer 450, and other wires that allow the controlling computer 450 to send the appropriate control signals to any electronics that is part of cup CP. In the main embodiment these wires are connected to an appropriate power supply controlled by the medical practitioner 420, and to the controlling computer 450, respectively. Alternative embodiments may have the light emitting device controlled by either a microcontroller or by a separate computer. Several other 420 friendly devices exist to allow the practitioner 420 to control and observe the position of the infrared emitter IR-emit (LE or 320). It is the intention of the inventor that the final product be made completely 420 friendly. Several variations of the hardware installed in the supporting device are possible, as variations to the main embodiment, particularly the inclusion of a single IR pixel detector, or an array of IR pixel detectors capable of detecting the back scattered photons, and of an array of emitting infrared emitter IR-emit (LE or 320), which would allow for infrared beams to be emitted either along many directions without rotating the supporting breast cup CP and/or parallel directions, at all or some positions along the supporting breast cup CP without rotating or translating the supporting breast cup CP.

This main embodiment with fixed "light" emitters LE (IR-emit or 320) produces an image with the spacial resolution equal to the distance between the fixed "light" emitters LE. If higher resolution is desired, it can be achieved with a modified cup CP of our invention, in which there is an approximately first conical supporting base that is in fixed position with respect to the breast BR, on which it is attached another, second supporting structure, which second supporting structure may be also conical, on which the light emitters (LE) and light detectors (LD) are mounted and an extra step: this second conical supporting structure is connected to the first conical supporting structure via motors capable of moving the second supporting structure on two non-collinear directions, say rotating this second supporting structure around the axis of the cone and also moving the second supporting structure along the length of the axis of the cone. Of course that any two other directions that are not collinear would be equally suitable, as x-y (Cartesian coordinates), and any other displacement.

Microcomputer 450 receives the data from either the pixel-type infrared detector IR-det or LD or from a possibly smaller number of individual detectors LD in fixed position with respect to the supporting structure, as shown in FIGS. 2, 3 and many others. Microcomputer 450 has suitable computer code to analyze the pixelized image transferred from the "light" detector LD (infrared detector IR-det) and determine the center of the "light" distribution. Microcomputer 450 will then construct two images: a transmitted image and a scattered image (see definitions at the definition section). The brightness of each pixel of the transmitted image is the numerical value of the measurement of the energy that reaches the infrared detector IR-det (LD) along the direction of the incident infrared beam IR-rad or LE-dir. This is so because the measurement on the pixel detector IR-det (LD) along the direction of the incident beam IR-rad (330) is the measurement of the energy that propagated through the breast BR without deviating from its original direction, that is, photons that did not suffer any scattering event. This assumption is an engineering approximation which is good enough because the probability of a photon suffering three or more scattering events such that at the end of the third (or more) scattering event it is along the initial direction is much to small to consider for the image process, as the reader will easily verify.

Examples of Intended Use

One intended use of my invention is an extra indicator of breast cancers in female humans. For breast cancer detection, it is easy to have a computer controlling both the illuminating beam and the detector, and also it is simple to keep both the illuminating IR beam mounted on the same supporting frame that holds the pixelized detectors, in which case the alignment between the illuminating beam and the pixelized detector is automatic and assured to stay constant. Breast cancers, like all other cancers eventually develop angiogenesis which increases the blood supply at the cancerous mass, which can be detected by infra red imaging. In other words: our invention detects angiogenesis (increase in blood supply), not cancer per se, but it is universally accepted that angiogenesis is a marker for cancer, so, detection of angiogenesis is a detection of cancer.

Another intended use of my invention is for teeth infra red imaging, which have many possible uses, all related to the blood supply. This use is simple because the hardware is small, and it is simple to keep the both the illuminating IR beam and the pixelized detectors mounted on the same supporting frame that holds both together. This simplifies the alignment between the emitting devices and the detecting devices that can then be held fixed and constant.

Another intended use of my invention is for tongue infra red imaging, which have many possible uses, all related to the blood supply associated with cancer detection. The hardware for tongue infra red imaging may be similar to the hardware used for teeth infra red imaging, with small modifications.

Another intended use of my invention is an extra indicator of other cancers in the abdominal cavity. Laparoscopy should use for this intended use, with both the infrared emitter IR-beam (330) and the pixelized detector introduced into the abdominal cavity using the standard procedures used in laparoscopy.

One intended use of the invention is for infrared images of the female breast. In this case the device would be detecting increased blood irrigation, which is one of the signatures of a cancerous mass, necessary for the faster cell growth (angiogenesis). If this document were not in danger of later being scrutinized by a damn lawyer, that will be looking to split hairs and distort statements, I would say here that all cancers, with the exception of leukemia, myeloma, and lymphoma, causes an increased blood supply at the cancerous mass, which then can be detected by its larger absorption and scattering cross-section (probability of) when compared with other animal cells.

Another intended use of the invention is for infrared images of the brain, possibly complementing EEG (Electro Encephalogram), MRI and fMRI (functional MRI), and others.

Another intended use of the invention is for infrared images of the tongue. In this case the device would be detecting increased blood irrigation within a potential cancerous mass.

Another intended use of the invention is for infrared images of the penis. In this case the device would be detecting increased blood irrigation within a potential cancerous mass.

Another intended use of the invention is for infrared images of the arm or leg. In this case the device would be detecting increased blood irrigation within a potential cancerous mass.

Another intended use of the invention is for infrared images of most parts of infants and small children, with smaller bodies when compared with adult bodies. In this case the device would be detecting increased blood irrigation within a potential cancerous mass at most parts of the body.

Another intended use of the invention is for infrared images of the teeth. In this case the device would provide information complementary to the currently used X-rays.

Operation of Invention

FIGS. 1A, 1B and 1C show a photon beam entering from the left, propagating to the right. As normal convention with vectors, the length of the arrow indicates the numerical value of the quantity (its magnitude), which in this case is the beam energy or any other equivalent quantity, as the number of photons, while the direction of the arrow indicates the propagation direction. FIG. 1A indicates the magnitude of the beam along its incident direction at 4 positions along the propagation direction: before entering the ellipsoidal object, just after entering the object, past halfway into the object, and after leaving the object. These four beams being along the same initial direction of propagation they indicate what we call the transmission beam, the beam along the initial propagating direction. The reader will notice that the size of the arrow gets progressively smaller, indicating that the beam intensity decreases as the beam moves along. This occurs because the beam is subject to scattering and to absorption, both of which decrease the beam intensity, so the incident beam is characterized by a progressively smaller intensity as it propagates.

FIG. 1B shows the same incident beam at left followed by three stages of progressively more scattering as the beam propagates forward. FIG. 1B is a highly simplified one, in that it fails to display what technically is known as the phase of the scattered beam, which can be simplified to be the position of the photon at each of the three indicated positions, which includes photons previously scattered and the photon just scattered at that point, or, in other words, photons at different points along each line representing scattered photons (that is, each "inclined" line). Ignoring this detail because it has is no consequence for the analysis that follows, we only mention here that we are making this over-simplification on FIG. 1B. The reader will notice that as the beam propagates forward, more and more photons are scattered, represented by larger arrows at any given direction. For example, the arrow representing scattering at 30 degrees to the right and forward becomes progressively larger from the second point to the third point (both inside the elliptical object) and finally to the last point outside of the object.

Finally, FIG. 1C shows all together, the transmitted and scattered photons (1C is a combination of 1A and 1B). It shows the transmitted beam decreasing in magnitude and the scattered beams increasing in magnitude along all directions. Of course that the scattering is on all angles around the incident direction, which means that in 3-D (3 dimensions) the scattering figures are to be seen as rotating the scattered beams around the incident beam axis.

In the main embodiment of our invention, a test for cancer starts with a transmission image obtained with the infrared emitter IR-emit (LE, or 320) propagating through a breast BR, one emitter at a time, say LEi to time ti. This "light" beam LB (really not visible light but preferentially an infrared beam) then suffers scattering and absorption as it propagates through the breast BR, and part of it, which does not suffer neither scattering nor absorption is detected at the "light" detector LDi that is aligned with the LEi that is emitting at that particular time ti. This measurement at "light" detector LDi is the intensity of the transmitted radiation (along that particular path of radiation) and becomes one pixel for the transmitted image (our name) Tij.

Likewise, other "light" detectors not aligned with LEi measure the intensity of the "light" that has suffered one or more scattering events and is propagating at a direction that is different than the initial direction of propagation. This "light" intensity, corresponding to the initial direction "i" is a pixel for the scattered image Sij.

The reader will notice that the transmitted image Tij and the scattered image Sij are two-dimensional matrices, as they ought to be, being, as they are, projection images of the object. Three images are produced by our invention: the transmitted image T, the scattered image S and the combined image C, this latter one being a mathematical merge of the transmitted image T and the scattered image S. The reader will take notice that it is not possible to just add the pixels of T to the pixels of S, because the transmitted image T is a negative image, in the sense of the old 35 mm photos, while the pixels of the scattered image S is a positive (or normal, so to say) image of the object. Foe example, a negative image can be produced of the transmitted image T in the following way:

1) define TNij as a normalized value of Tij as:

$TNij = Tij/\mathrm{MAX}(Tij)$, where MAX(Tij)=maximum value of any Tij
So that $0 <= TNij <= 1$ Then the negative of TNij can be defined as $TNNij = 1 - TNij$, so that $0 <= TNNij <= 1$.

After similar normalization of Sij the two images (TNNij and Sij) could be added in the ordinary way, because both are positive images. There are many other ways to do similar procedures that add the two images, which is a very well known to the mathematicians, and we will not enter in this tipic here, but only highlight that it is not good to just add Tij to Sij because they will "oppose" each other.

Along some of these directions along the "light" beams LB that propagate through the breast of a patient, there may exist a cancer. The cancer, which is more irrigated by blood than the surrounding cells, which in turn causes that there is more absorption of infrared radiation and also more scattering, will appear in matrix T, when its values are displayed on monitor 410, as a darker region (more absorption and scattering, therefore less transmission), and in matrix S, when its values are displayed on monitor 410, as a brighter region (more scattering). Figures FIG. 2a and FIG. 2b are examples of such images in two possible representations which correspond to the familiar geographic representations of the planet Earth known as Mercator projection (FIG. 2a) and Mollweide or pseudocylindrical map projection (FIG. 2b). Many other projections can be used, and the main embodiment of our invention provides programs to display most of the best known projections at the choice of medical practitioner 420, which he/she choses using controls at keyboard 440 to suite his/her preferences. As known to mathematicians knowledgeable in the art, the change between these projections is a straightforward mathematical manipulation with a known mathematical formula, generally easy to implement in computer 450.

Finally, FIG. 14 is a block diagram of the software running the system in one of its implementations.

Technical Information:

infrared emitter: preferred wavelength: 800 to 900 nm, preferred beam diameter: 1 mm, preferred beam waist: 0.3 mm, preferred power: 300 mW, Infrared detector: preferred number of pixels: 50 by 50 pixels, 2,500 pixels total, any other number of pixels being possible. Also individual detectors, as per FIGS. 2, 3, etc.

Description and Operation of Alternative Embodiments and Improvements

Variations of the Invention

An interesting variation of the main embodiment is to have the inside of the breast cup of our invention in contact with the female breast while the light emitters LE and light detectors LD are not fixed with respect to the breast cup, but are rather movable, under computer control, with respect to the breast cup. In this variation the breast cup still has windows pressed against the subject breast, keeping the soft breast tissue parallel and in direct contact with the outer side of the windows, while the light emitters LE emit light perpendicular to the windows. This way the light beams propagating from the light emitters LE are incident on the side 1, or inner side, of the windows W at a normal incidence (zero degrees) and exit the window at the side 2, or outer side, also at normal incidence, then enter the breast tissue at normal incidence as well, given that the breast surface is pressed against the outer surface of the window W and light detectors LD. This arrangement has the advantage that the light emitters can move within the limits of the size of the windows W, preferably, but not necessarily only all together, which increases the resolution of the instrument because each window will generate several pixels for image, instead of one single pixel if the windows are fixed with respect to the light emitters LE, one light emitter for each window.

One possible improvement of my invention is to add a collimator in front of the "central detector". FIGS. 6 and 7 shows one example of such a collimator. Observing FIG. 7 the reader will notice that radiation that have suffered one or more scattering events may still propagate in the direction of the "central detector", but, if it is along any direction different than the initial propagating direction, which is the direction of the collimating tube, this radiation will be absorbed at the wall of the collimator CL. Collimator CL prevents such cases from causing incorrect readings by the "central detector". The walls of the collimator CL would be of such a surface that absorbs the type of radiation used for the image, which, in the main embodiment is infrared at 850 nm. The wall may have also other characteristics to stop scattering at the walls as well, which is not part of our invention here.

One possible variation of my invention is to have a rotating motor to perform the rotation of inserting tube 350, and/or a translating motor to perform the translation of same.

It may be also possible to use the system of my invention for transmission and scattering images of all parts of the abdominal cavity with a laparoscopic procedure. In this case, though it is more invasive than the main embodiment, which requires no cut on the patient and no sedation, the procedure may prove an additional method for cancer detection when a laparoscopy is already decided upon, in which case nothing extra is required when compared with the procedure already decided. It is worth to note than often a laparoscopy is made just as an inspection to confirm the existence of a cancer, in which case my invention would offer another extra information. For example, samples may be taken for laboratory examination (pathology laboratory), but samples are not normally taken in excess, to avoid tissue injure, possible blood losses, etc. An image, on the contrary, can be as extensive as desired, because it causes no injury. This way samples could be taken from the highly suspicious parts of the abdominal cavity, while infrared images could be taken of much wider regions and parts of the abdomen.

Other applications of my invention are to investigate the physical characteristics of some hidden part, as a gasoline tank, a jet engine and the like. These objects, like any other, have different reflectances, transmittances and scattering properties, which vary with wavelength. Therefore, images as described in the main embodiment can be made in all available wavelengths, each contributing to a different information on the characteristic of the object. This is particularly true for wavelengths that are easily accessible with diode lasers and/or with LED (light emitting diodes), but other sources are also possible, using a fiber optics to introduce the light inside the hidden part of the object.

As written above, all that is described for the head applies in a very similar way for the female breast, which is also a curved surface with different optical properties then the air, and similarly to the head the solution is a liquid or paste with matching index of refraction (matching optical properties) inside a containing structure that has a flat outer surface. With such a container the first transmission is from air to the index of refraction of the glass or plastic or any other material transparent to the radiation used, which occurs at normal incidence, and therefore the "light" beam direction is preserved upon refraction into the glass or plastic, then the exit surface of this glass or plastic container has also parallel sides which are also perpendicular (normal) to the direction of the "light" beam propagation, which ensures that the "light" beam continues along the same direction upon leaving the exit surface and entering the liquid or paste, which is made to be of the same index of refraction as the entry surface into the patient, usually the skin. Therefore then the second transmission is from the glass or plastic to the liquid, also at normal incidence, and from there on the index of refraction is the same until the other side of the head or the breast, where the process repeats itself on the opposite direction.

Alternatively, the containing structure with a flat outer surface which is normal (remember that normal means perpendicular in optics) to the propagating "light"

CONCLUSION, RAMIFICATIONS, AND SCOPE OF INVENTION

The principle of operation stems from Maxwell's equation (REF Reitz, Milford and Christy, "Foundations of Electromagnetic Theory" (1980), sect 18.2 ff., pg. 385 ff., particularly FIGS. 18-3 and 18-4). Some of the consequences of the boundary conditions applied to electromagnetic radiation, including infrared radiation, that propagates from a medium 1 to a medium 2 is that fraction of radiation (or percentage) that is reflected back into the initial medium 1 and the fraction (or percentage) of radiation that is refracted, transmitted into medium 2. Both depend on the electro-magnetic properties of each medium, on the angle of the electric field with the local surface of incidence and with the direction of polarization, and both are proportional to the difference between the indices of refraction of the two media, tending to 0 (zero) as the difference between the indices of refraction goes to 0 (zero).

Our invention also discloses a plurality of infrared emitters, each of a substantially small size, say, from 100 micrometers to 1 mm, but these are preferred sizes, so, for the lawyers out there, other larger sizes being also possible, other larger sizes not invalidating my beautiful invention. These smaller sized emitters are seen at FIGS. 8, 9, 10, 11, 6, 7, 12, 13. With this embodiment there is no need to use wedge W2, because the support structure is made malleable with the consequence that the infrared emitters are automatically adjusted to emit perpendicular to the surface or to the skin of the patient undergoing infrared examination. Likewise the "light" detectors LD are, in this embodiment, touching the surface, or the skin of the patient, obviating the problem of change of direction of propagation of the infrared radiation as it exits the body of the patient.

Figure 8:
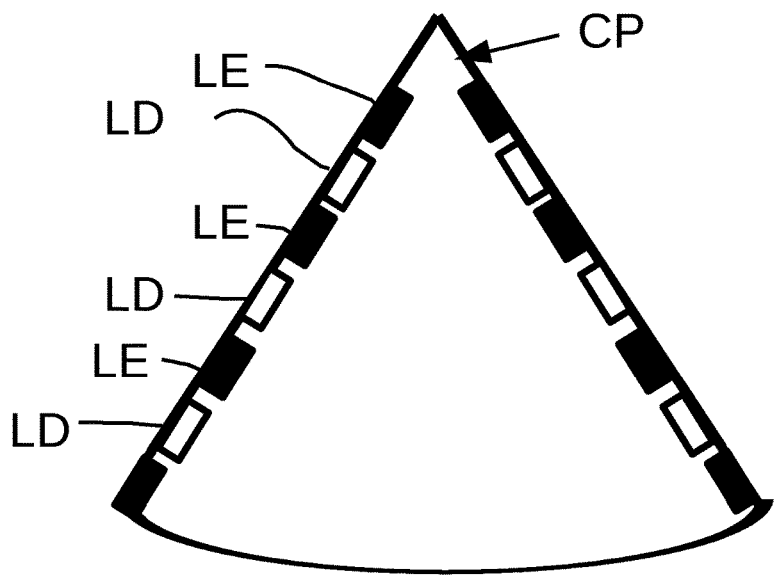

Several variations are possible. For example, the shape of cup CP can take any shape still within the scope of the invention. Cup CP may be a standard cylinder, as shown in FIGS. 8, and 9, or cup CP may take the shape of a truncated cylinder capped by a smaller cylinder, as shown at FIG. 10, or cup CP may take the shape of a truncated cylinder capped by a curved surface at the vertex of the cylinder, as shown at FIG. 11. These shape variations are common, as a casual observation of shapes and sizes of women's bras shows: they come in an endless variety of shapes and sizes but they are still bras. Likewise with our incredibly beautiful invention, which works with an endless variety of cups CP sizes and shapes.

An important variation for the physical positioning of the light detector LD is shown at FIGS. 6 and 7, where 7 is a detail of one of the light detectors LD in 6. 6 and 7 depict recessed light detectors LD, which are set back (that is, towards or even totally outside cup CP) to allow for the inclusion of a light collimator LC (shown in FIG. 7 only) along the path from the object to the light detector LD. FIG. 7 also shows a possible light "ray" along the correct direction to reach light detector LD at the end of collimator LC. This correct direction is the direction of emission from a light emitter LE at the other side of the breast, or, the direction of emission of the light emitter LE that is paired with the particular light detector LD cum collimator.

Another possible positioning for the light emitters LE, or for the light detectors LD, or for both (as shown in FIG. 12) is the direction of LE, the direction of LD or both (as depicted in FIG. 12). It does not matter the direction of the light emitters, as long as the computer knows their position and direction of emission. Of course that if LD are fitted with collimators, as per FIGS. 6 and 7, then the associated light emitters LE need to be aligned with the collimators.

An important part of the devices described here is the use of an array of "light" emitters and "light" detectors used to create the image. We emphasize here that, as explained earlier, we use the word "light" to encompass all the electromagnetic spectrum, from radio waves to X-ray, including light and infrared. There are two different options for this: option 1 is an array consisting of "light" emitters and "light" detectors arranged in the same structure at different locations, perhaps on a regular array, as an x-y array, or a circular array, etc., and option 2 is two different arrays, one for the "light" emitters and another array for the "light" detectors.

As described elsewhere, the invention depends on a scanning beam, which is difficult to make because it depends on moving the "light" beam by a precise amount, the accuracy of this motion determining the accuracy of the image, which is difficult to implement. An alternative solution is to have a fixture fixed with respect to the object, this fixed fixture having several light beam emitters at the desired direction and angular position, preferably a large number of light beam emitters. This is easy to implement with current technology. In other words this embodiment discloses an emitter device fixed with respect to the object, the emitter device being fitted with an array of emitters, perhaps on an x-y arrangement (an array, a square or rectangular array or any other configuration). This way, instead of moving the beam, which entails mechanical problems, the supporting structure for the emitter can stay stationary, while the emitter that has just emitted "light" is turned off and another emitter, is turned on, which causes another light beam to impinge on the object without moving the supporting structure. The new emitter can be next to the one that just went dark or in any other position, as long as the controlling computer knows which is the new emitter that is turned on—that is, knows the direction and position of the new beam. The advantage of this arrangement is that it forestall the need for a complex structure that is capable of moving the beam with good accuracy of displacement and beam orientation. FIG. 12 shows one such array, while FIGS. 8, 9, 10, 11, 6, 7, and 13 also show such array, but in these figures only the light emitters LE and "light" detectors LD that are positioned on the side of the supporting structure are seen, all others, as the "light" emitters and "light" detectors facing the viewer are not shown for clarity.

Another variation of the above fixture with multiple light emitters is to add amplitude modulation to the light emitters, in such a way that each light emitter is amplitude modulated at a different enough frequency as to be distinguishable from each other. In laymen terminology, it is similar to all radio stations transmitting simultaneously, as they do, yet each of them emitting at its particular assigned frequency, which frequencies are assigned to be separated enough from each other that each station is separable from the others at the radio receiving end, which, as we all know, allows the listener to select the particular radio station that she/he wants to listen out from all signals that enter the radio receiver. In a similar way, each "light" emitter can be amplitude modulated at a particular frequency and each one of the "light" detectors can "listen" to each of the "light" emitters, one at a time. In this case the separation can be done with the technique of lock-in amplification, which is a well known technique, better than what is used in radio receivers, and widely used in research laboratories the world over. This variation of each light emitter emitting "light" amplitude modulated at its particular frequency, allows for simultaneous signal detection by all emitters at the same time, with a gain in the time required to obtain the image.

The reader will notice that the fixture that holds the "light" emitters and "light" detectors in place shown at FIGS. 8, 9, 10, 11, 6, 7, 12, etc. are either conical or at least near conical. This is because they are adapted to be used in women's breast and this general shape, if the cone is just smaller then the breast, causes that when pressed into position all the "light" emitters LE and "light" detectors LD are touching the skin and also pressing against the breast tissue, leaving no air pockets in between. This is so to prevent unwanted refractions from air to human tissue (different indexes of refraction), which would change the direction of the light beam in an uncontrollable way. The reader will notice that with the design proposed and the "light" emitters LE and "light" detectors LD fixed in place and direction and a stiff supporting structure, the position of the "light" beams is known and predictable, as needed for the latter processing of the data. Moreover, the beam is produced then emitted normal (perpendicular) to the window at the exit part of the "light" emitter, which ensures that the refraction is also at 0 degrees (zero degrees).

Still another variation of the above fixture is to have the supporting fixture strong and stiff enough to resist deformations due to normal handling and stress due to normal use, yet also including accommodation to allow both the "light" emitters and "light" detectors to move perpendicularly to their direction of "sight" in order that the external surface of each touch and stay in direct contact with the skin of the patient, to avoid the "light" transmission to go through an air layer in between them, which air layer might cause a non-normal incidence between the patient's skin and the air layer, which would cause a change in direction of the "light" "ray" (by "ray" here we mean the direction of propagation, which is the "ray" of common parlance, not in scientific parlance). The reader will appreciate that having the "light" emitter and "light" detector able to move in-and-out along its direction of "light" emission and "light" detection, so that the outer surface of the external window is flush with the patient's skin causes a normal incidence on the patient's skin, which, in turn, according to Snell's law causes that the angle of transmission, that is, the angle of "light" propagation inside the patient's body is 0 degrees (zero degrees), that is, no deviation from the incident direction. Such an in-and-out movement may be accomplished with many methods, for example, a spring at the bottom of each "light" emitter and each "light" detector, or an inflatable supporting structure which is pressurized when the supporting structure is in place, which would force each unit to move out until stopped by the patient's skin, etc. Another way to understand the objective of this variation is that as the pieces, "light" emitter and "light" detectors, are squeezed out from the supporting structure against the breast, or other tissue, the flesh and skin adjust to the external object, becoming flush to this external object, in this case with the "light" emitters and detectors. The supporting structure would, as shown in the figures, be already near the shape of the desired body part, as a conical supporting structure is for a breast cancer screening device. Such conical shapes are shown at FIGS. 8, 9, 10, 11, 6, 7, 12, etc.

Still another variation is the inclusion of a "light" collimator, as shown in FIGS. 6 and 7. These collimators are useful to prevent off-line photons to reach the detector and be counted as non-scattered photons, which are, by necessity along the initial emission direction. These "light" detectors with collimators are the detectors in front of some "light" emitter, intended to measure the amount of non-scattered "light" that went through the object, from one side to the other. Other "light" detectors, not directly in front of some "light" emitter, are not necessarily fitted with such collimator, because these "light" detectors are allowed to measure all the "light" coming from any direction, after any number of scattering events. These detectors with collimators should not count scattered light coming from any other direction other than the initial emission direction, so these collimators are at least good, some may say necessary, for an accurate measure of the non-scattered photons. The length and diameter of the collimators determine the angular acceptance of the "light" detector at the end of the collimator, the angular acceptance being a value to be determined on a case-by-case depending on the type and quality of image desired.

Still many other variations are possible for the supporting device, which is a conical shape when made for use as a breast scanning, to be flat, or small curvature, or a deformable surface, as a bed sheet, or a rod, depending on the application, with "light" emitters and "light" detectors on the same side of the object under scanning. This is possible because scattering occurs in all directions, including back onto the direction of the incoming "light" beam (see physics definition of forward and back scattering). If the reader doubt this, she/he only has to think about driving at night inside a fog: light emitted forward from the headlights is scattered back to the eyes of the vehicle driver, which is the reason why high beams are worse than useless in a fog, there being more back scattered light by the fog itself than from any object ahead that the driver would like to avoid hitting, as a tree, etc. It is also worth pointing out how this effect depends on the wavelength of the light used, which is the reason why light for fog is amber/yellow: amber/yellow color back scatters less than other colors. Back on our invention, such images with back scattered "light" are useful in locations where it is difficult, or even impossible, to have "light" emitters on one side of the object and "light" detectors on the opposite side of the object, as for a breast scanner.

Sequence Listing * #$^{PPA}$

Not applicable.

The invention claimed is:

1. An infrared tissue imaging apparatus for tissue blood concentration, comprising:
   a cup shaped support structure arranged to conform the tissue to be imaged,
   an at least one infrared radiation emitter LE configured to emit radiation beams each, along an incident direction which defines a line of path of the incident photons, each said radiation beam causing a measurement along said incident direction that is a single point Tij for a transmitted image, each said single point Tij of said transmitted image associated with the position of said single incident direction,
   an at least one infrared radiation detector LD, each one said radiation detector LD being configured to measure a radiation intensity along said line of path of said incident photons of one of said radiation emitters LE that emits radiation propagating along said line of path of said incident photons, which determines one pixel element for a transmitted image Tij,
   computer connected to the emitter and the detector and configured for controlling both the radiation emitter illuminating beam and the radiation detector,
   wherein the emitter and the detector are fixed on the cup shaped support structure,
   where said radiation detectors LD that lie along said same line of path of said incident photons said radiation emitted by said at least one radiation emitter LE, which create one said individual pixel for a transmitted image Tij, are in fixed position with respect to said radiation emitters LE and are fitted with a collimating section CL that prevents radiation from entering said radiation detector LD, unless it is mostly along said direction at which said radiation was emitted by said radiation emitter LE,
   the computer configured for collecting all measurements of said radiation intensities Tij measured by said radiation detectors LD measuring said radiation intensity Tij along said direction of said radiation beam emitted by said radiation emitters LE on the matrix T which contains the information for a complete first transmitted image,
   the computer further configured to construct two images (1) a transmitted image and/cup or (2) a scattered image Sij by analyzing pixelized image transferred from detector and determine the center of the light distribution associated with brightness of each pixel of the transmitted image is the numerical value of the measurement of the energy that reaches the infrared detector,
   displaying said values of Tij and/or on a display to create a first transmitted image T and/or a second scattered image S of an object OBJ.

2. The apparatus of claim 1 where the radiation emitter LE and the radiation detector LD are attached to a supporting structure SS enveloping the totality or part of the object OBJ.

3. The apparatus of claim 2 where the structure SS enveloping the totality of part of the object OBJ is shaped as a conical structure and the object OBJ is a female breast.

4. The apparatus of claim 1 where said first transmitted image T displays the local relative amount of blood in the object.

5. The apparatus of claim 1 where said first transmitted image T displays suspected cancerous masses.

* * * * *